(12) United States Patent
Buehler et al.

(10) Patent No.: US 12,376,852 B2
(45) Date of Patent: Aug. 5, 2025

(54) WOUND CREATION FOR EXCESS SKIN REMOVAL AND CLOSURE SYSTEMS AND METHODS

(71) Applicant: Osheru, Inc., Bend, OR (US)

(72) Inventors: Patricia Buehler, Bend, OR (US); Brian Bowman, Carlsbad, CA (US); Daivon Deans, El Cajon, CA (US); Benjamin Arnold, San Diego, CA (US); Knute Buehler, Bend, OR (US)

(73) Assignee: Osheru, Inc., Bend, OR (US)

( * ) Notice: Subject to any disclaimer, the term of this patent is extended or adjusted under 35 U.S.C. 154(b) by 34 days.

(21) Appl. No.: 18/140,984

(22) Filed: Apr. 28, 2023

(65) Prior Publication Data

US 2023/0346375 A1 Nov. 2, 2023

Related U.S. Application Data

(60) Provisional application No. 63/336,861, filed on Apr. 29, 2022.

(51) Int. Cl.
*A61B 17/072* (2006.01)
*A61B 17/29* (2006.01)

(52) U.S. Cl.
CPC .... *A61B 17/072* (2013.01); *A61B 2017/2926* (2013.01)

(58) Field of Classification Search
None
See application file for complete search history.

(56) References Cited

U.S. PATENT DOCUMENTS

| 1,401,190 A | 12/1921 | Sheridan |
| 2,679,249 A | 5/1954 | Maximiliano |
| 3,054,398 A | 9/1962 | Kobler |

(Continued)

FOREIGN PATENT DOCUMENTS

| WO | 1998000069 A1 | 1/1998 | |
| WO | WO-9800069 A1 * | 1/1998 | ........... A61B 17/062 |
| WO | WO-2023212330 A1 | 11/2023 | |

OTHER PUBLICATIONS

International Search Report and Written Opinion from PCT App. No. PCT/US2023/020421 dated Sep. 21, 2023, 16 pages.

(Continued)

*Primary Examiner* — Tanzim Imam
(74) *Attorney, Agent, or Firm* — COOLEY LLP

(57) ABSTRACT

Excess skin removal and wound closure devices, such as blepharoplasty devices and methods, are provided. An exemplary device for excising excess skin (e.g. eyelid skin) and creating wound closure includes a base, a lever mechanism coupled with the base via a lever pivot, a locking mechanism, an elongate curved first jaw member in fixed relationship with the base and having a lower serrated tissue contacting surface, an elongate curved second jaw member in movable relationship with the base and having an upper serrated tissue contacting surface. The upper serrated tissue contacting surface of the second jaw member can face toward the lower serrated tissue contacting surface of the first jaw member. The locking mechanism can be releasably engageable with the second jaw member. The pivoting actuation of the lever mechanism can cause linear movement of the second jaw member relative to the first jaw member.

23 Claims, 31 Drawing Sheets

(56) References Cited

U.S. PATENT DOCUMENTS

| | | | |
|---|---|---|---|
| 3,766,925 A * | 10/1973 | Rubricius | A61B 17/122 606/120 |
| 4,321,916 A | 3/1982 | McKee | |
| 4,542,742 A | 9/1985 | Winkelman et al. | |
| 4,557,265 A | 12/1985 | Andersson | |
| 4,644,651 A | 2/1987 | Jacobsen | |
| 4,917,677 A * | 4/1990 | McCarthy | A61B 17/30 606/151 |
| 5,070,860 A | 12/1991 | Grounauer | |
| 5,498,256 A | 3/1996 | Furnish | |
| 5,534,008 A | 7/1996 | Acksel | |
| 5,728,112 A | 3/1998 | Yoon | |
| 5,984,934 A | 11/1999 | Ashby et al. | |
| 6,283,913 B1 | 9/2001 | Seibel | |
| 6,346,078 B1 | 2/2002 | Ellman et al. | |
| 6,626,922 B1 | 9/2003 | Hart et al. | |
| 7,146,895 B2 | 12/2006 | Kong et al. | |
| 7,252,667 B2 | 8/2007 | Moses et al. | |
| 7,384,421 B2 | 6/2008 | Hushka | |
| 8,876,859 B2 | 11/2014 | Buehler et al. | |
| 2005/0033356 A1 | 2/2005 | Frank et al. | |
| 2007/0244516 A1 | 10/2007 | Chiu et al. | |
| 2010/0010537 A1 | 1/2010 | Warren | |
| 2012/0149990 A1 * | 6/2012 | Buehler | A61B 17/28 606/201 |
| 2016/0262750 A1 | 9/2016 | Hausen et al. | |
| 2016/0262827 A1 | 9/2016 | Ross | |
| 2020/0054340 A1 * | 2/2020 | Armenteros | A61B 17/0643 |

OTHER PUBLICATIONS

Angres, "A simple approach to blepharoplasty using the Angres II blepharopigmentation lid clamp," Ann Ophthalmol. 1988, 20(9), pp. 349-351.

Office Action for U.S. Appl. No. 13/324,920 dated Mar. 28, 2014, 7 pages.

Fredriksson et al., "New mechanical device for effective removal of skin tags in routine health care," Dermatology Online Journal, 2009, 15(2): 9, 15 pages.

Invitation to Pay for International Application No. PCT/US2023/020421 dated Jun. 27, 2023, 2 pages.

Keyhani et al., "Modified technique and ptosis clamp for surgical correction of congenital pediatric ptosis by anterior levator resection," Facial Plast Surg. 2007, 23(3), pp. 156-161.

Office Action for U.S. Appl. No. 13/324,920 dated Nov. 7, 2013, 11 pages.

Notice of Allowance for U.S. Appl. No. 13/324,920 dated Jul. 10, 2014, 5 pages.

Seltzer, "A new fenestrated instrument for blepharoplasty for upper eyelid," J Natl Med Assoc. 1976, 68(3), pp. 217-218.

Small et al., "A New Upper Blepharoplasty Clamp," Ophthalmic Plast Reconst Surg. 1985, 1, pp. 103-105.

International Preliminary Report on Patentability for International Application No. PCT/US2023/020421 mailed Nov. 7, 2024, 13 pages.

* cited by examiner

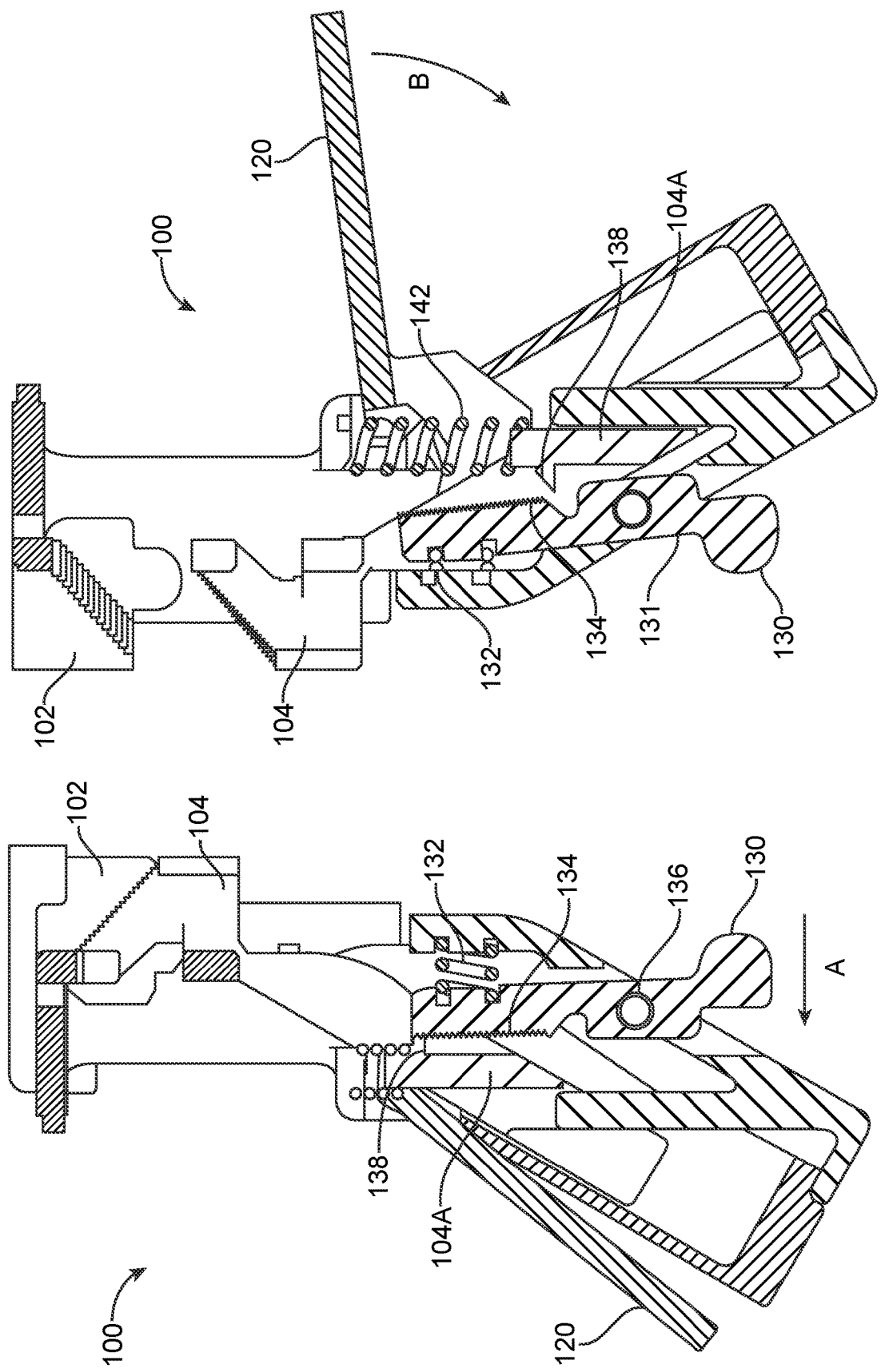

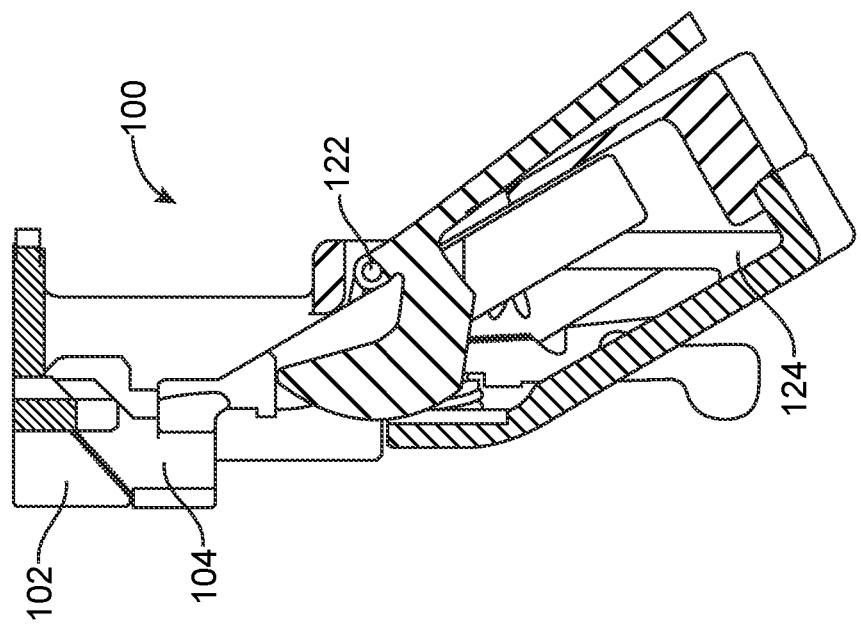
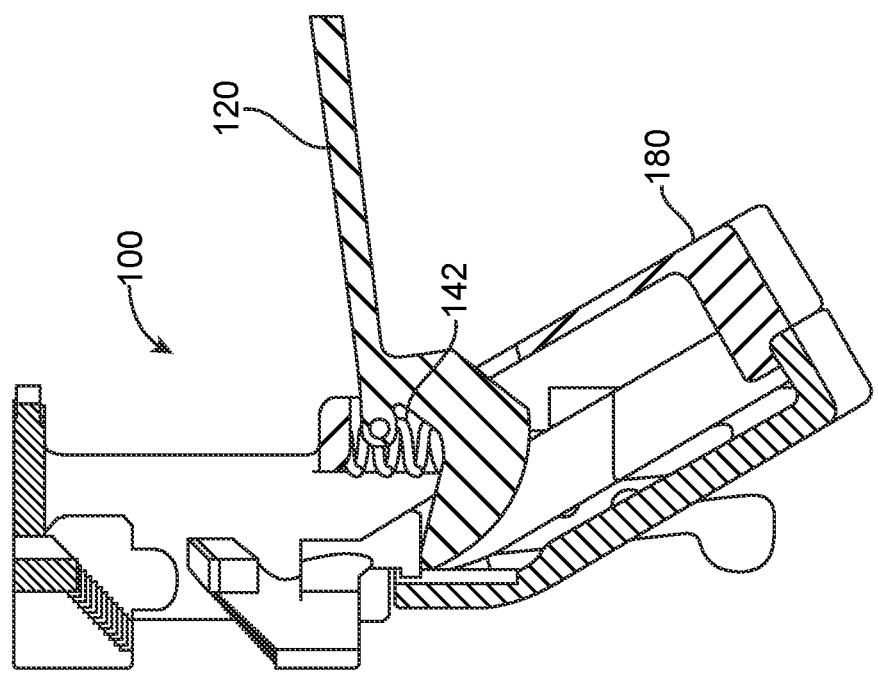
FIG. 5A
FIG. 5B

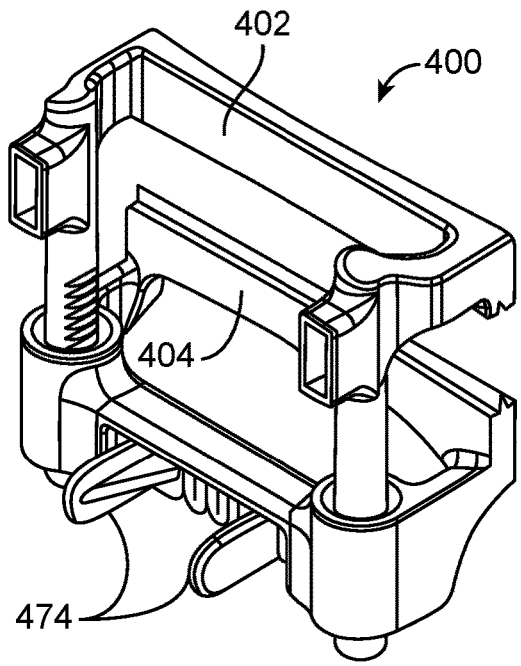 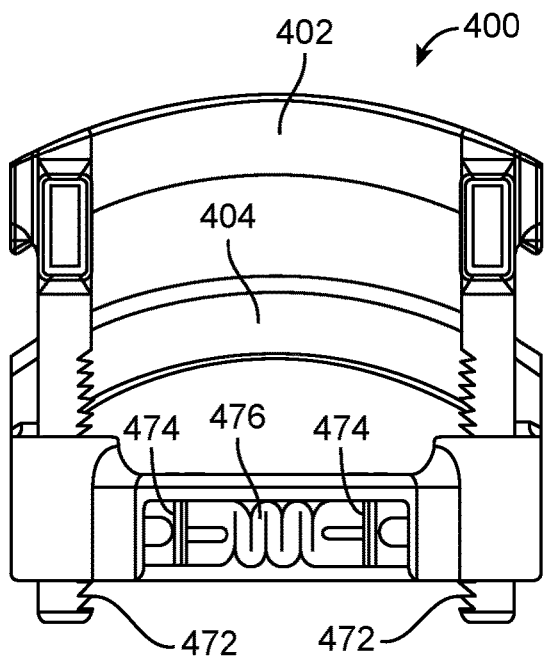
FIG. 14A  FIG. 14B
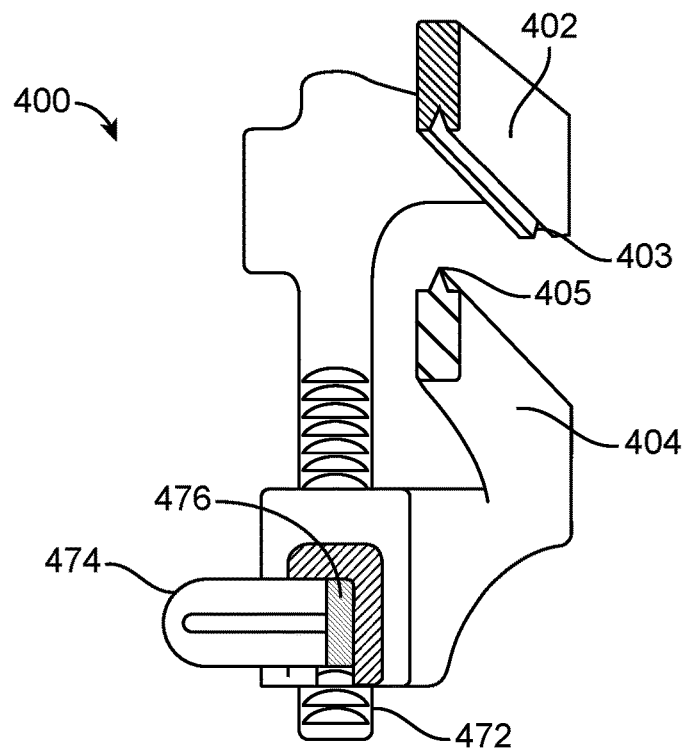
FIG. 14C

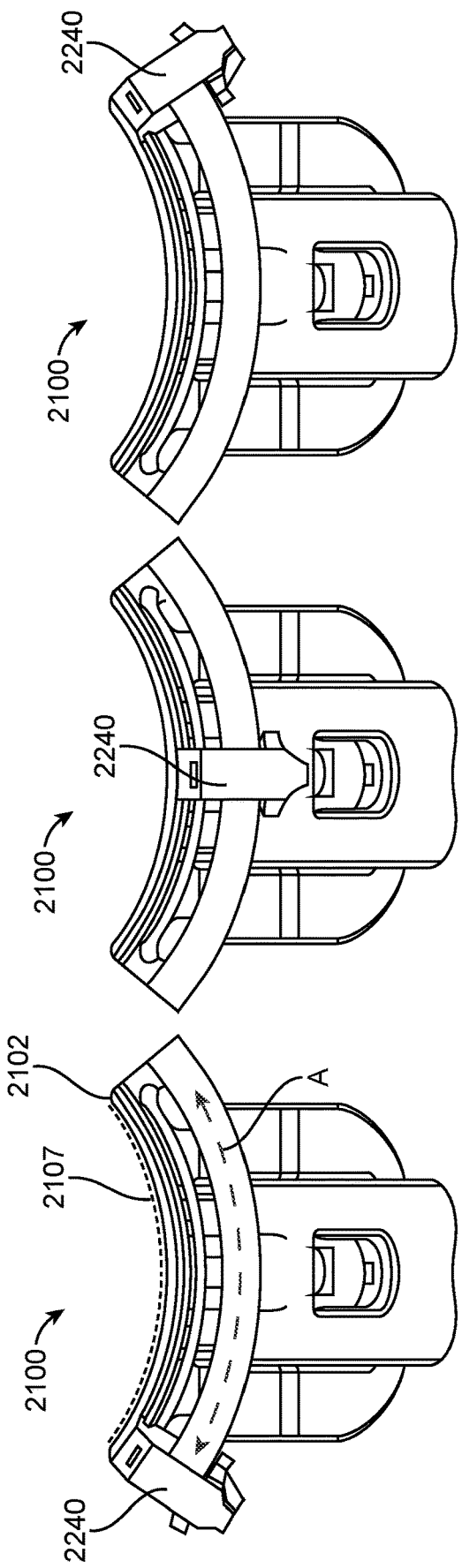

WOUND CREATION FOR EXCESS SKIN REMOVAL AND CLOSURE SYSTEMS AND METHODS

CROSS-REFERENCES TO RELATED APPLICATIONS

This application claims the benefit of U.S. Provisional Patent Application No. 63/336,861 filed Apr. 29, 2022, the disclosure of which is incorporated herein by reference.

BACKGROUND

The present disclosure relates to systems and methods for creating a wound to remove excess skin and closing wounds, and in particular embodiments relates to devices for performing blepharoplasty and methods for using the same.

Blepharoplasty is a surgical procedure that removes excess skin and/or fat from the eyelids of a patient. The surgery is performed on patients who have excess eyelid skin and desire removal for aesthetic reasons and/or for functional reasons, such as to improve the peripheral vision of individuals whose upper eyelids have drooped into their field of vision.

To address excess upper eyelid skin, the surgeon can remove a segment of skin in the upper eyelid and then suture the edges of the resulting incision together. The surgery is generally performed under local anesthesia and/or intravenous or oral sedation, and typically takes between one and two hours for the surgeon to perform.

Good cosmetic and functional results are dependent on the location of the incision and removal of the proper amount of excess skin tissue. Symmetry is desirable to achieve a pleasing result, hence the surgeon generally attempts to remove a similar amount of tissue from each upper eyelid.

Conventional blepharoplasty procedures suffer from several deficiencies. 1) surgical planning and marking of the patient is needed to assure that a symmetric and aesthetically pleasing result will occur, 2) the surgery can take an hour to perform, 3) injection of local anesthesia can swell and distort the tissue, 4) there is bleeding requiring cautery, 5) meticulous, time consuming suturing is required, 6) post-operatively the patient can have disfiguring bruising and swelling for two to three weeks, 7) the patient must limit activity and put ice on the lids for several days, 8) the patient needs to return for suture removal, and 9) the patient can have post operative complications including wound dehiscence, suture granulomas and asymmetry.

Currently available blepharoplasty systems and methods provide good results for patients, however improvements in blepharoplasty technology are desired. Likewise, currently available devices and methods for removing excess skin and closing wounds provide good results for patients, however improvements in excess skin removal and wound closure technology are desired. Embodiments of the present invention can, for example, make such procedures easier and faster for the surgeon, avoid the need for intravenous or oral sedation, local anesthesia injection, cautery, and suturing of the wound. Such procedures can be offered at lower cost and be less invasive with faster healing for the patient, thus solving some of the deficiencies in the current blepharoplasty procedure, as well as in the current excess skin removal and wound closure procedure.

BRIEF SUMMARY OF THE INVENTION

Embodiments of the present invention are directed to systems and methods for removing excess skin and closing wounds, and in particular embodiments, encompass devices for performing blepharoplasty and methods for using the same.

Although embodiments of the present invention relate specifically to blepharoplasty systems and methods, it is understood that any aspect, component, feature, or process discussed herein in relation to blepharoplasty can likewise be incorporated, in a broader sense, into exemplary excess skin removal and wound closure systems and methods, and such excess skin removal and wound closure systems and methods also equally encompassed by the instant disclosure.

Exemplary embodiments encompass devices for creating and closing upper eyelid wounds as well as other types of wounds. In some cases, such wounds may be created using any of the devices and/or methods disclosed herein (e.g. using jaws and a cutting mechanism). In some cases, such wounds may be of various sizes and shapes. In some cases, such wounds may be on various areas of a patient's body. For example, exemplary systems and methods can be used for removing excess skin and closing wounds in the sagging chin area, the sagging forehead area, the sagging breast area, the sagging under arm skin, and the like. In some cases, exemplary devices used to close such wounds can include jaws and a cutting device to create and zipper-lock seal such wounds using any of the embodiments disclosed herein. In some cases, exemplary devices can embody various sizes, shapes, and/or curvatures to fit into or engage with these various areas of the body. In some cases, exemplary wound closure systems and methods can be used to close traumatic wounds by bringing the edges of the wound together, and sealing them with the jaws to take tension off the traumatic wounds so they may be able to be effectively closed with tissue glue rather than sutures. For such applications, devices of various sizes and curvatures can be used, optionally in conjunction with an adjustable set of jaws, to accommodate variable size wounds.

Blepharoplasty is a common procedure done in a surgical operating room or an outpatient setting (office suite). Surgeons may typically take 1-2 hours to perform the procedure, use IV or oral sedation and local injection of anesthetics, and require use of cautery and sutures. The patient can experience significant post-operative bruising, swelling and disfigurement that commonly lasts 2-3 weeks. The patient must return for suture removal and can have complications including wound dehiscence, suture granuloma, and asymmetry. Exemplary blepharoplasty systems and methods disclosed herein can enable the surgeon to complete the procedure in less than an hour, cost significantly less, can be completed in an outpatient setting without IV or oral sedation or injection of local anesthesia, cautery, or sutures, resulting in a faster recovery for the patient with less bruising and swelling than the current standard of care.

Embodiments of the present invention encompass excess skin removal and wound closure systems, including without limitation blepharoplasty systems, having a (1) skin marker with ruler, (2) disinfectant, (3) topical anesthetic, (4) a grasping tool with an elongated surface contacting area and serrations to pull and prepare skin tissue for clamping and cutting off blood flow to tissue desired for removal, (5) eyelid lift device has serrations and ratchet mechanism or latch mechanism which compresses and seal excess skin, (6) cutting mechanism to excise the unwanted skin, and (7) bonding agent to close incision. In some cases, a ratchet mechanism or latch mechanism can be referred to as a locking mechanism. In some cases, a locking mechanism can operate to lock the device in the closed position. Exemplary excess skin removal and wound closure system devices, including without limitation blepharoplasty system devices, can have serrations that clamp the skin and create a desired skin configuration for cutting. Embodiments disclosed herein encompass excess skin removal and wound closure systems, including without limitation blepharoplasty system, having a cutting mechanism attachable to a blepharoplasty or other excess skin removal and wound closure device which provides the removal of the excess skin tissue. Exemplary excess skin removal and wound closure systems, including without limitation blepharoplasty systems, include a lever mechanism to allow actuating jaw at various distances and allow adjustment of the skin tissue subject for removal. In some cases, an excess skin removal and wound closure system, including without limitation a blepharoplasty system, can include a ratchet mechanism that allows actuating jaw locking at various distances and allows adjustment of the skin tissue subject for removal. Embodiments disclosed herein encompass excess skin removal and wound closure systems, including without limitation blepharoplasty systems, having marking components, a local topical anesthetic, an iodine swab, and an incision bonding agent to allow the procedure to be completed quickly (e.g. within 10 minutes) after the anesthesia is complete. An incision bonding agent can be included in an excess skin removal and wound closure system, including without limitation a blepharoplasty system, to provide sealing of the incision. Exemplary excess skin removal and wound closure systems, including without limitation blepharoplasty systems, can include a grasping tool with serrations to enhance the manipulation of tissue. A grasping tool can have an elongated body and a narrow section for fitting through an excess skin removal and wound closure device, including without limitation a blepharoplasty device, from the anterior direction and expanding to grab or grasp and pull the tissue through. Exemplary excess skin removal and wound closure systems, including without limitation blepharoplasty systems, include a kit to complete the full procedure.

In a first aspect, embodiments of the present invention encompass a device to excise excess skin and create wound closure. An exemplary device can include a base, a lever mechanism coupled with the base, a locking mechanism, an elongate, curved first jaw member in fixed relationship with the base and having a lower tissue contacting surface, and an elongate, curved second jaw member in movable relationship with the base and having an upper tissue contacting surface, where the upper tissue contacting surface of the second jaw member facing toward the lower tissue contacting surface of the first jaw member. Pivoting actuation of the lever mechanism can cause movement of the second jaw member relative to the first jaw member. The locking mechanism can be configured to maintain the first jaw member and the second jaw member in fixed relationship relative to one another. In some cases, the lower tissue contacting surface is serrated, and the upper tissue contacting surface is serrated. In some cases, the lever mechanism is coupled with the base via a lever pivot. In some cases, pivoting actuation of the lever mechanism causes linear movement of the second jaw member relative to the first jaw member. In some cases, the locking mechanism is releasably engageable with the second jaw member. In some cases, the locking mechanism is coupled with the base via a locking pivot. In some cases, the device further includes a latch mechanism, and the locking mechanism is releasably engageable with the latch mechanism. In some cases, the locking mechanism releasably engages the latch mechanism at a location that is within the base. In some cases, the latch mechanism is coupled with the second jaw member. In some cases, the device includes a latch spring that is compressible between the latch mechanism and the base. In some cases, the latch spring biases engagement of the latch mechanism against the locking mechanism. In some cases, the locking mechanism is coupled with the lever mechanism. In some cases, the device includes a pawl in fixed relationship with the second jaw member, where the locking mechanism includes engagement teeth configured to releasably engage the pawl. In some cases, the device includes a locking spring configured to bias the engagement teeth of the locking mechanism against the pawl. In some cases, at least one of the first jaw member or the second jaw member includes a silicone coating. In some cases, the device includes an actuating jaw spring configured to bias the second jaw member away from the first jaw member. In some cases, the device includes a lever actuating torsion spring configured to bias the second jaw member away from the first jaw member. In some cases, at least one of the first jaw member or the second jaw member includes a tissue contacting side having a contoured surface with a shape that is customized to the anatomy of a patient based on an imaging scan of the patient.

In another aspect, embodiments of the present invention encompass a skin removal and wound closure device that includes a base, a lever mechanism coupled with the base via a lever pivot, a locking mechanism, an elongate, curved first jaw member in fixed relationship with the base and having a lower serrated tissue contacting surface, and an elongate, curved second jaw member in pivoting relationship with the lever and having an upper serrated tissue contacting surface, where the upper serrated tissue contacting surface faces toward the lower serrated tissue contacting surface of the first jaw member. The locking mechanism can be releasably engageable with a support assembly of the first jaw member. A pivoting actuation of the lever mechanism can cause linear movement of the second jaw member relative to the first jaw member. In some cases, the locking mechanism includes a first set of engagement teeth and a second set of engagement teeth that releasably engage the support assembly of the first jaw member. In some cases, the locking mechanism includes a serpentine section that enables compression of the locking mechanism. In some cases, the device includes a jaw actuation handle spring coupled with the base and the lever mechanism. In some cases, the support assembly of the first jaw member is releasably engageable with the base. In some cases, the locking mechanism includes one or more locking mechanism compression tabs.

In a further aspect, embodiments of the present invention encompass a method of performing an excess skin removal and wound closure procedure. An exemplary method may include grasping tissue of a patient with a grasping tool, positioning the tissue between an upper jaw mechanism and a lower jaw mechanism of an excess skin removal and wound closure device, pivoting a lever of the excess skin removal and wound closure device relative to a base of the excess skin removal and wound closure device, so as to cause advancement of the lower jaw mechanism toward the upper jaw mechanism, thereby clamping the tissue therebetween, creating an incision in the tissue, and removing a portion of the tissue from the patient. In some cases pivoting the lever of the excess skin removal and wound closure device relative to the base of the excess skin removal and wound closure device causes linear advancement of the lower jaw mechanism toward the upper jaw mechanism. In some cases, a method can include applying a bonding agent to the incision. In some cases, a method can include inserting the grasping tool between the upper jaw mechanism and the lower jaw mechanism of the excess skin removal and wound closure device prior to grasping the tissue with the grasping tool. In some cases, the positioning step can include removing the grasping tool from between the upper jaw mechanism and the lower jaw mechanism of the excess skin removal and wound closure device. In some cases, the lever pivots relative to a support assembly of the upper jaw mechanism when the lever pivots relative to the base. In some cases, the lever slides relative to a support assembly of the upper jaw mechanism when the lever pivots relative to the base. In some cases, a method can include locking the lower jaw mechanism in place relative to the upper jaw mechanism prior to creating the incision. In some cases, the locking step includes pivoting a locking mechanism of the excess skin removal and wound closure device. In some cases, the locking step includes compressing a locking mechanism of the excess skin removal and wound closure device. In some cases, the grasping tool includes a distal end having microneedles.

In another aspect, embodiments of the present invention encompass blepharoplasty devices, which may be used to remove excess eyelid skin tissue from a patient's eyelid. Exemplary blepharoplasty devices may include a base, a lever mechanism coupled with the base via a lever pivot, and a locking mechanism. Devices may also include an elongate, curved first jaw member in fixed relationship with the base and having a lower serrated tissue contacting surface, and an elongate, curved second jaw member in movable relationship with the base and having an upper serrated tissue contacting surface. The upper serrated tissue contacting surface of the first jaw member can face toward the lower serrated tissue contacting surface of the second jaw member. The locking mechanism can be releasably engageable with the second jaw member. Pivoting actuation of the lever mechanism can cause linear movement of the second jaw member relative to the first jaw member. In some cases the second jaw member includes a shield restricting movement of the cutting mechanism perpendicular to actuation path. In some cases, the locking mechanism is coupled with the base via a locking pivot. In some cases, devices can include a pawl in fixed relationship with the second jaw member. The locking mechanism can include engagement teeth configured to releasably engage the pawl. In some cases, devices can include a locking spring configured to bias the engagement teeth of the locking mechanism against the pawl. In some cases, devices can include an actuating jaw spring configured to bias the second jaw member away from the first jaw member. In some cases, a device can include a torsion spring configured to adjust the lever mechanism to bias the second jaw member away from the first jaw member.

In another aspect embodiments of the present invention encompass blepharoplasty devices having a base, a lever mechanism coupled with the base via a lever pivot, a locking mechanism, an elongate curved first jaw member in fixed relationship with the base and having a lower serrated tissue contacting surface, and an elongate curved second jaw member in pivoting relationship with the lever and having an upper serrated tissue contacting surface. The upper serrated tissue contacting surface of the second jaw member can face toward the lower serrated tissue contacting surface of the first jaw member. The locking mechanism can be releasably engageable with a support assembly of the first jaw member. In some cases, the locking mechanism can be releasable engageable with the lever mechanism. Pivoting actuation of the lever mechanism can causes linear movement of the second jaw member relative to the first jaw member. In some cases, the locking mechanism includes a first set of engagement teeth and a second set of engagement teeth that releasably engage the support assembly of the first jaw member. In some cases, the locking mechanism includes a serpentine section that enables compression of the locking mechanism. In some cases, the locking mechanism includes an engagement latch that can releasably engage the lever mechanism. In some cases, devices include a jaw actuation handle spring coupled with the base and the lever mechanism. In some cases, a support assembly of the first jaw member is releasably engageable with the base. In some cases, a locking mechanism includes one or more locking mechanism compression tabs.

In still a further aspect, embodiments of the present invention provide methods of performing a blepharoplasty procedure. Exemplary methods may include grasping eyelid tissue of a patient with a grasping tool, positioning the eyelid tissue between an upper jaw mechanism and a lower jaw mechanism of a blepharoplasty device, pivoting a lever of the blepharoplasty device relative to a base of the blepharoplasty device, so as to cause linear advancement of the lower jaw mechanism toward the upper jaw mechanism, thereby clamping the eyelid tissue therebetween, creating an incision in the eyelid tissue, and removing a portion of the eyelid tissue from the patient. In some cases, methods can include applying a bonding agent to the incision. In some cases, methods can include inserting the grasping tool between the upper jaw mechanism and the lower jaw mechanism of the blepharoplasty device prior to grasping the eyelid tissue with the grasping tool. In some cases, the positioning step can include removing the grasping tool from between the upper jaw mechanism and the lower jaw mechanism of the blepharoplasty device. In some cases, the lever pivots relative to a support assembly of the upper jaw mechanism when the lever pivots relative to the base. In some cases, the lever slides relative to a support assembly of the upper jaw mechanism when the lever pivots relative to the base. In some cases, methods can include locking the lower jaw mechanism in place relative to the upper jaw mechanism prior to creating the incision. In some cases, the locking step can include pivoting a locking mechanism of the blepharoplasty device. In some cases, the locking step can include compressing a locking mechanism of the blepharoplasty device.

In some embodiments, a blepharoplasty device may include silicone coated jaws. The presence of silicone can operate to reduce the ability for the jaws to adhere to skin, allowing the ability to seal the incision with adhesive while the skin is clamped within the jaws.

These and other embodiments are described in further detail in the following description related to the appended drawing figures.

BRIEF DESCRIPTION OF THE DRAWINGS

Specific embodiments of the disclosed device, surgical systems, or methods will now be described with reference to the drawings. Nothing in this detailed description is intended to imply that any particular component, feature, or step is essential to the invention.

FIGS. 4A and 4B depict aspects of an excess skin removal and wound closure device, in accordance with some embodiments of the present invention.

FIGS. 5A to 5D depict aspects of an excess skin removal and wound closure device, in accordance with some embodiments of the present invention.

FIGS. 14A to 14D depict aspects of an attachable cutting mechanism, in accordance with some embodiments of the present invention.

FIGS. 21A to 21C depict aspects of an excess skin removal and wound closure device, in accordance with some embodiments of the present invention.

DETAILED DESCRIPTION OF THE INVENTION

Figure 1B:
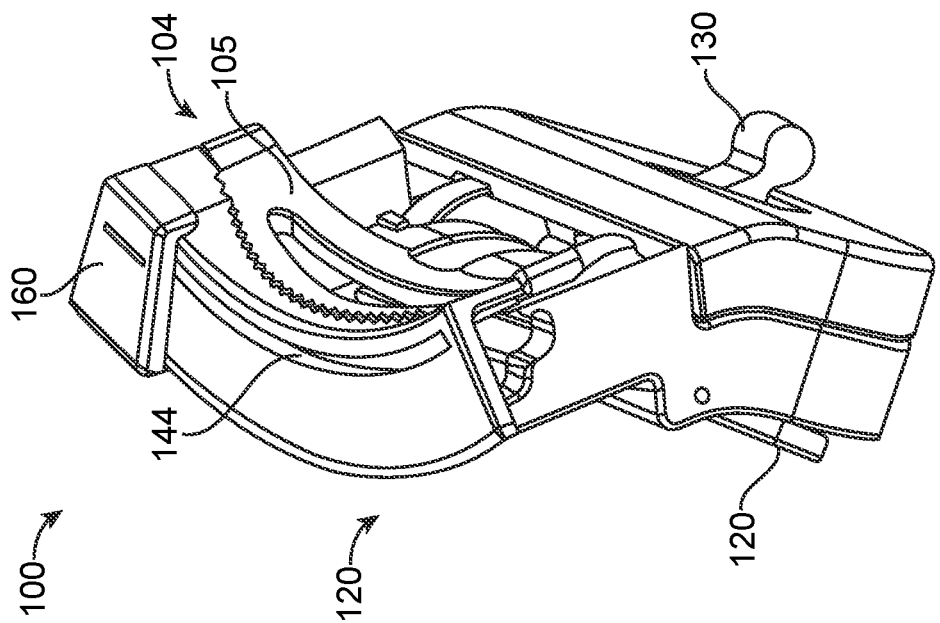
FIGS. 1A and 1B depict aspects of an excess skin removal and wound closure device, in accordance with some embodiments of the present invention.

Various embodiments of blepharoplasty devices and their methods of use are disclosed herein. The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the singular forms "a," "an," and "the' include the plural forms unless the context clearly dictates otherwise. Additionally, the term "includes' means "comprises." Further, the term "coupled" generally means electrically, electromagnetically, and/or physically (e.g., mechanically or chemically) coupled or linked and does not exclude the presence of intermediate elements between the coupled or associated items absent specific contrary language. As used herein, the term "superior" means toward the top of the head of a patient and "inferior" means toward the feet of a patient.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

The devices and methods disclosed herein can generally improve the overall efficiency of a blepharoplasty procedure by simplifying the steps required to perform a blepharoplasty procedure, enhancing the consistency of the procedure, and/or promoting faster healing and less disfigurement of the patient after the procedure.

Blepharoplasty is a common plastic surgery procedure done in a surgical operating room although some procedures available in an outpatient setting (office suite). Surgeons may typically take 1-2 hours to perform the procedure with an elevated cost comparable to the outpatient setting. Post operation from procedures in the surgical operation room can take 2-3 weeks with disfiguring bruising and swelling. Exemplary blepharoplasty systems and methods disclosed herein can enable the surgeon to complete the procedure in less than an hour, cost significantly less, can be completed in an outpatient setting, and involves faster recovery and less bruising and swelling than the current standard of care.

Exemplary blepharoplasty procedures disclosed here can involve marking the area of the eyelid tissue desired for removal with a marker and providing a topical anesthetic to temporarily anesthetize the surgical area. After the surgical area is fully anesthetized, the surgical site can be disinfected with an iodine swab. A grasping tool (e.g. forceps) can enter through the open jaws of the device, compress into the closed position, grasp the marked eyelid skin tissue area, and then pull the tissue through the open jaws of the device. One of the device jaws can then actuate into the closed position, fully clamping the tissue and cutting blood flow. A cutting mechanism can then be used to cut the eyelid skin tissue off. In some cases, a cutting mechanism is integrated with the blepharoplasty device. In some cases, a cutting mechanism can be a separate device for use subsequent to the clamping of skin tissue by the blepharoplasty device. After excess tissue is removed, an incision bonding agent can be applied on the incision, sealing it and allowing it to heal.

Figure 1A:
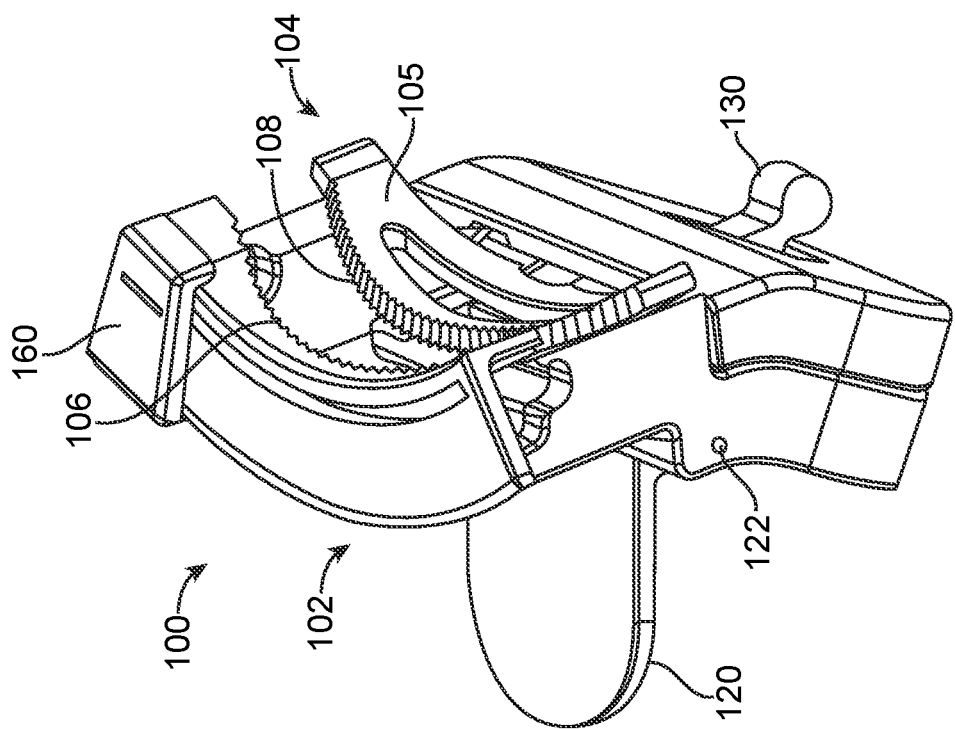
Figure 16B:
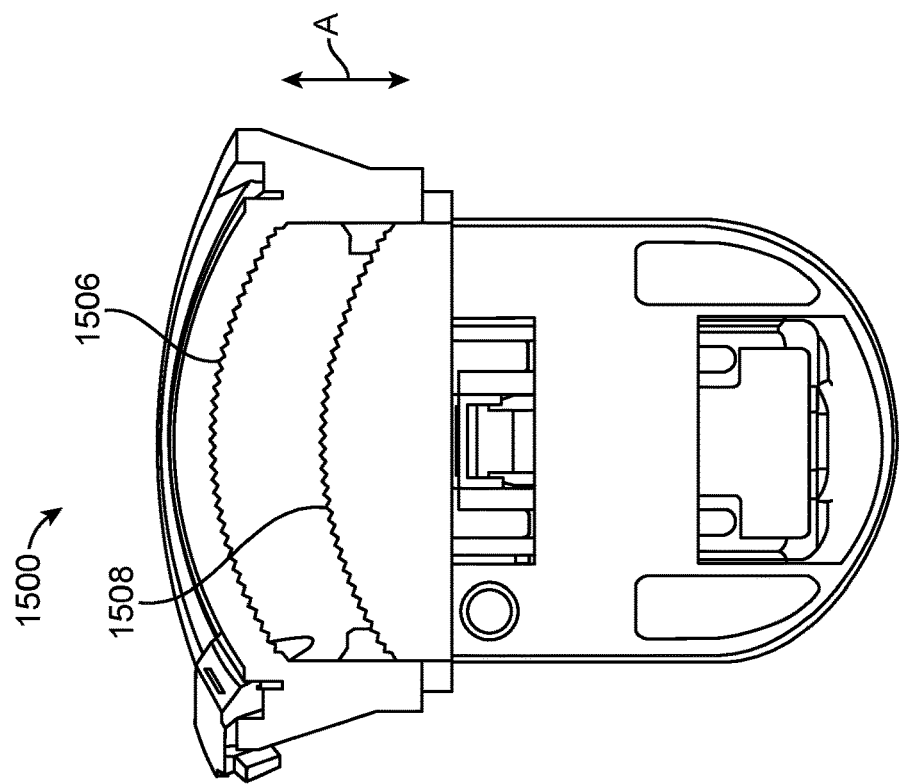
FIGS. 16A and 16B depict aspects of an excess skin removal and wound closure device, in accordance with some embodiments of the present invention.
Figure 16A:
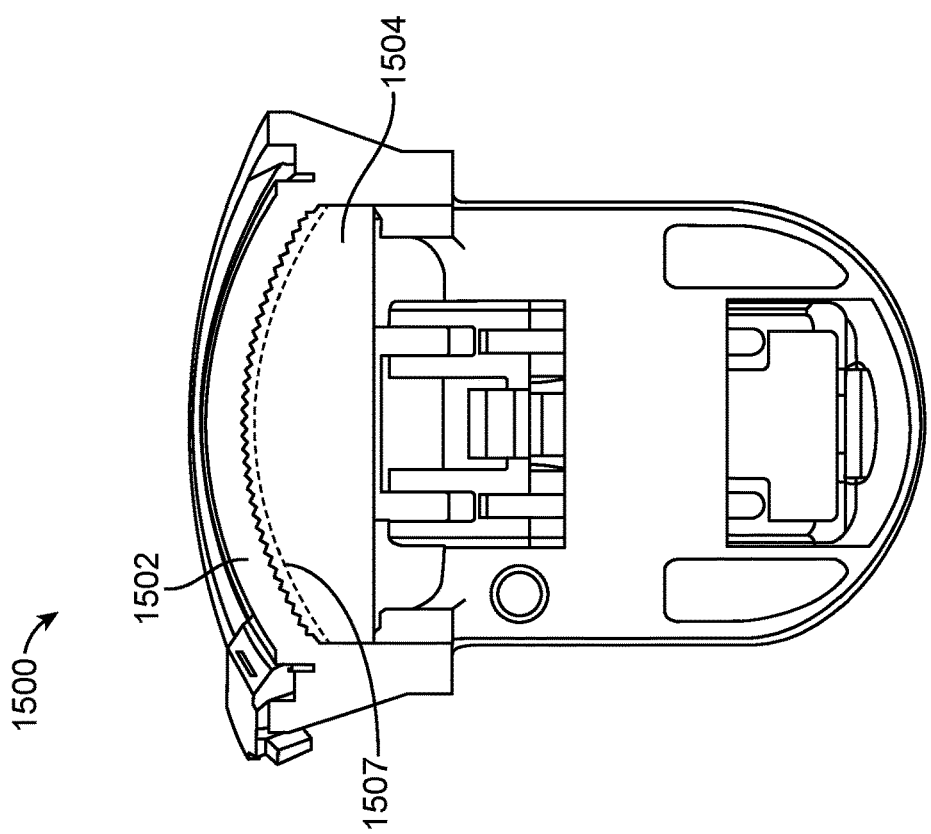

Turning now to the drawings, FIGS. 1A and 1B illustrate an embodiment of a blepharoplasty device 100 that is configured to capture eyelid tissue to facilitate tissue excision from a portion of an eyelid. Device 100 is a tissue gripping device (e.g. a clamp) comprised of a pair of elongated jaw members 102, 104 operatively connected together so that they can be moved relative to one another between an open position (FIG. 1A) and a closed position (FIG. 1B). Upper jaw members 102 and lower jaw member 104 can be curved to follow a contour of the eyelid area to produce a desired incision shape. In some embodiments, a jaw member can have a superoinferior curve of radius 1⅜ inches and an anteroposterior curve of radius 1⅝ inches to establish contour. With reference to FIGS. 16A and 16B, jaw member 1502 (or a tissue contacting surface 1506 thereof) has a superoinferior curve 1507 (dashed line). In some embodiments, the superoinferior curve corresponds to this arch 1507, which is within the plane of the drawing sheet and raised in the center and lowered on each side, for example as opposed to a curve relative (perpendicular) to the plane of the drawing sheet, where the center is farther away from the viewer and each side is closer to the viewer. With reference to FIG. 21A, a jaw member 2102 (or a tissue contacting surface thereof) has an anteroposterior curve 2107 (dashed line). In some embodiments, the anteroposterior curve corresponds to this arch 2107, which is within the plane of the drawing sheet and lowered in the center and raised on each side, for example as opposed to a curve relative (perpendicular) to the plane of the drawing sheet, where the center is closer to the viewer and each side is farther away from viewer. In some cases, the contour created is established from patient anatomy imaging using photographs, computerized tomography (CT) scans, or data or information from other imaging devices.

In some embodiments, the upper jaw member would be considered the superior jaw member and the lower jaw member would be considered the inferior jaw member because of their relative positions with respect to the head and feet. For purposes of simplicity, the terms "upper" and "lower" are used herein to refer to the superior and inferior members, although it should be understood that "upper" and "lower" do not imply any positional relationship aside from the anatomical reference points of the body.

Upper jaw member 102 has a first tissue contacting surface 106 and lower jaw member 104 has a second tissue contacting surface 108. First and second tissue contacting surfaces 106, 108 generally face one another in an opposing manner so that when eyelid tissue is positioned between upper and lower jaw members 102, 104, first and second tissue contacting surfaces 106, 108 can move towards one another to capture and secure the eyelid tissue between the first and second tissue contacting surfaces 106, 108.

When upper jaw member 102 and lower jaw member 104 are in the open position (FIG. 1A), first and second tissue contacting surfaces 106, 108 are separated by a distance to form an opening or space that is large enough to receive eyelid tissue. As upper and lower jaw members 102, 104 move together to the closed position (FIG. 1B), the distance between first and second contacting surfaces 106, 108 is reduced to a smaller distance. With this smaller distance, the opening or space between first and second tissue contacting surfaces 106, 108 is small enough to capture and secure any eyelid tissue positioned between first and second tissue contacting surfaces 106, 108.

First and second tissue contacting surfaces 106, 108 are configured to grip and hold eyelid tissue that is positioned between the opposing first and second tissue contacting surfaces 106, 108. Device 100 also includes a cutting member or cutting mechanism slider 160. A cutting mechanism slider 160 can include or be coupled with a cutting blade (not shown) and the blade can be moved along and/or within a blade guide 144. As shown here, blade guide 144 can be a curved slit, track, or edge along the upper jaw 102. Advantageously, as further discussed herein, such a cutting mechanism can actuate in the medial lateral directions through skin tissue, for the removal of a desired amount of skin tissue. In some embodiments, lower jaw member 104 may be referred to as an actuating jaw. As shown in FIGS. 1A and 1B, actuating jaw 104 may include a tissue contacting side 105. Device 100 may also include an actuating jaw lever 120, and a locking mechanism 130 such as a ratchet mechanism post. Embodiments of the present invention encompass devices having a ratchet mechanism to allow actuating jaw locking at various distances and allow adjustment of the skin tissue subject for removal. In some cases, a locking mechanism can be attached to an actuating handle component of the device.

Hence, embodiments of the present invention provide unique blepharoplasty system, including related devices, kits, and methods for the removal of eyelid skin tissue and the sealing of incised skin. Exemplary devices can include two curved serrated skin contacting jaws with one jaw fixed (e.g. upper member 102) and one jaw actuating (e.g. lower member 104), whereby the configuration of the device can be alternated between a closed position (e.g. FIG. 1B) and an open position (e.g. FIG. 1A), in which the open position allows eyelid skin tissue to protrude in between the jaws and the closed position clamps the skin tissue restricting blood flow to the eyelid skin tissue. An actuating mechanism can include a lever 120 with a pivot 122, whereby actuation of the actuating jaw lever 120 about the pivot 122 enables an adjusting of the linear position of the actuating jaw 104 relative to the fixed jaw 102 (e.g. between open configuration shown in FIG. 1A where lever 120 is in an upward position, and closed configuration shown in FIG. 1B where lever is in a downward position).

In some cases, an actuating jaw 104 can be releasably coupled with a ratchet mechanism 130 allowing the distance between jaws 102, 104 to be locked in various distances between fully opened (e.g. 8 mm) and fully closed (e.g. 0 mm). A ratchet mechanism 130 can include a mechanism to release the coupling of the ratchet mechanism allowing the re-adjustment of the actuating jaw 104. As further discussed elsewhere herein, in some embodiments, a device can include or be configured to operate in association with a cutting attachment, and the cutting attachment can include an actuating mechanism to cut the clamped eyelid skin tissue.

In some embodiments, a blepharoplasty device may include silicone coated jaws (e.g. jaws 102, 104). The presence of silicone can operate to reduce the ability for the adhesive to adhere to the jaws of the device, allowing the ability to seal the incision with adhesive while the skin is clamped within the jaws.

Figure 2B:
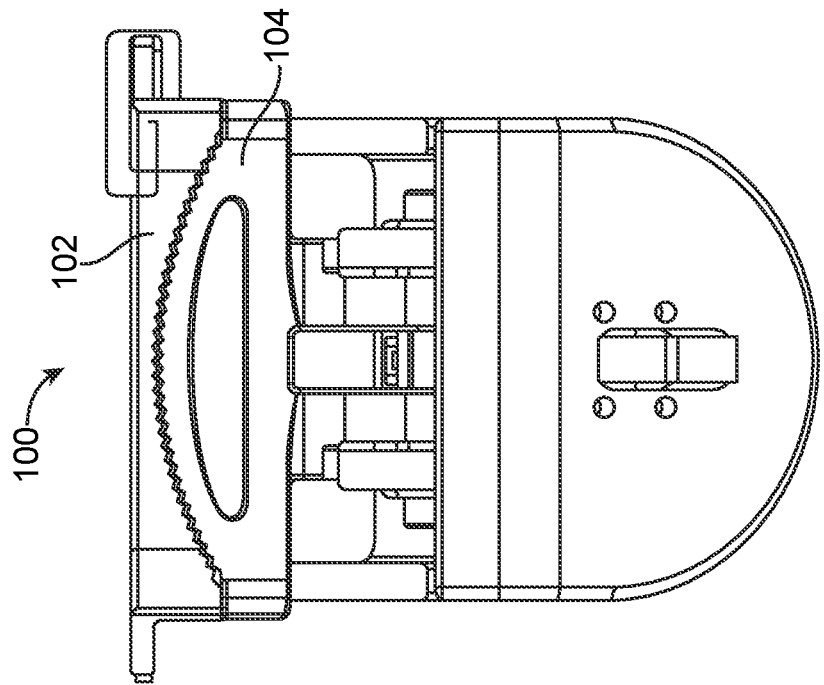
FIGS. 2A and 2B depict aspects of an excess skin removal and wound closure device, in accordance with some embodiments of the present invention.
Figure 2A:
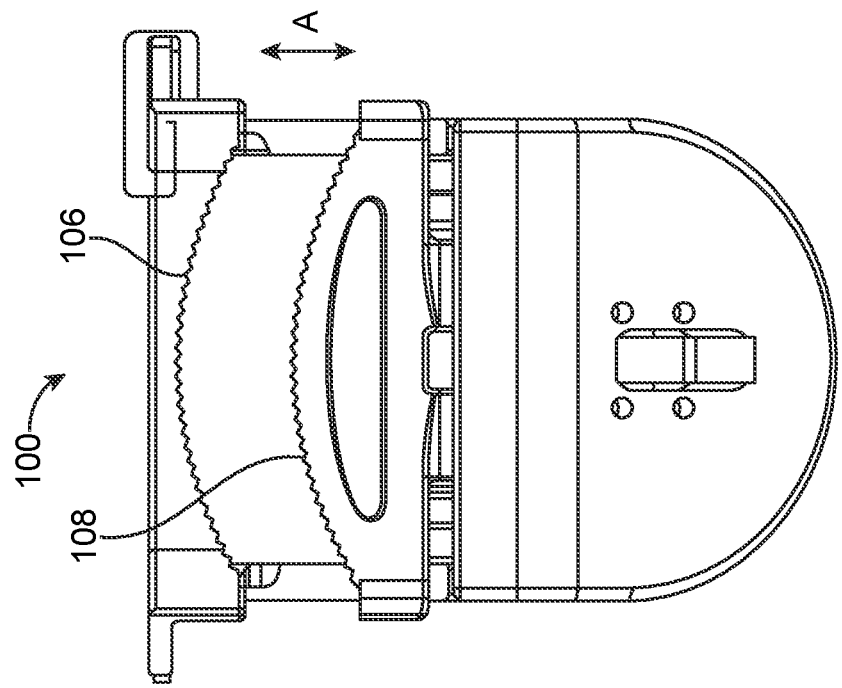

FIGS. 2A and 2B provide additional views of device 100 in an open position or configuration (FIG. 2A) where upper and lower jaws 102, 104 are farther apart, and in a closed position or configuration (FIG. 2B) where upper and lower jaws 102, 104 are closer together. Alternating between the open and closed configurations can involve linear movement of the lower jaw 104 relative to the upper jaw 102, as indicated by arrow A. First and second contacting surfaces 106, 108 can have serrated edges. Hence, embodiments of the present invention encompass devices having jaws with serrations to allow the clamped skin to crush onto itself creating a desired site for cutting. Serrations can be interlocking allowing the skin tissue to deform to the point that the desired amount of skin for removal remains protruded and the skin remains crushed after the clamp has released.

Figure 3B:
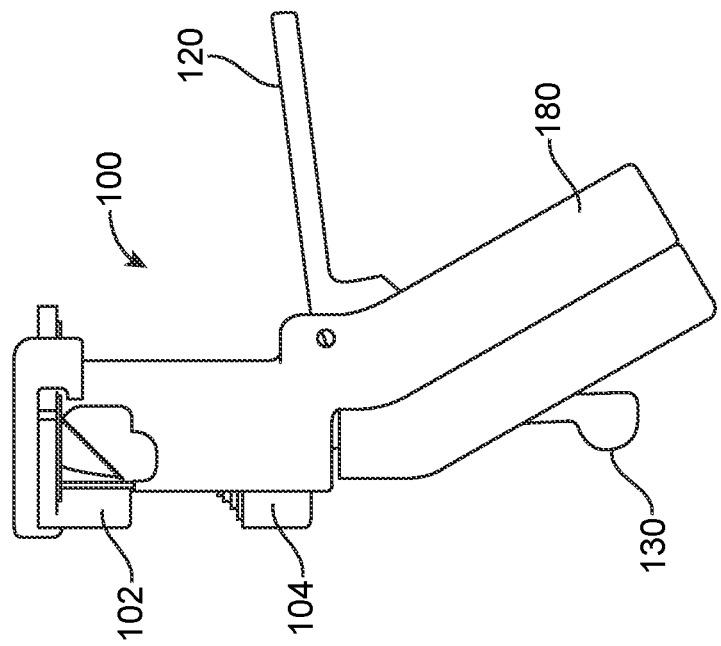
FIGS. 3A and 3B depict aspects of an excess skin removal and wound closure device, in accordance with some embodiments of the present invention.
Figure 3A:
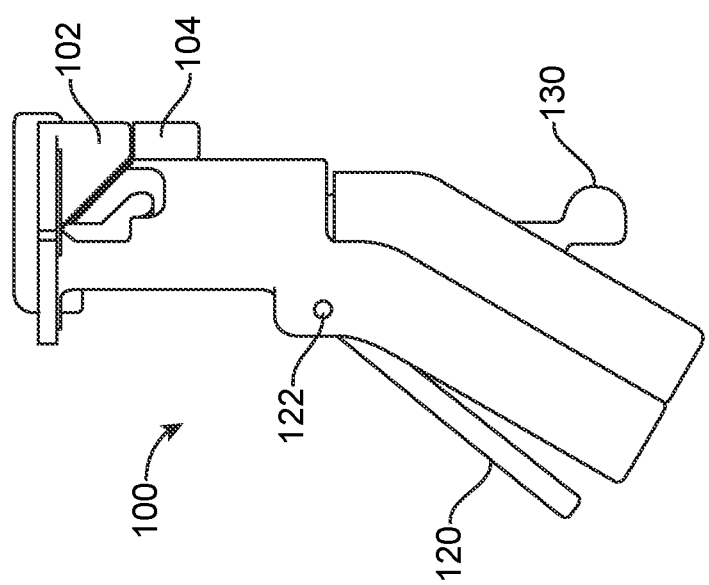

FIGS. 3A and 3B provide additional views of device 100 in a closed position or configuration (FIG. 3A) where upper and lower jaws 102, 104 are closer together, and in an open position or configuration (FIG. 3B) where upper and lower jaws 102, 104 are farther apart. Device 100 can include an actuating jaw lever 120 and a locking mechanism 130 such as a ratchet mechanism post. Pivot 122 enables actuating jaw lever 120 to pivot relative to a base 180 of the device 100.

FIGS. 4A and 4B provide additional views of device 100 in a closed position or configuration (FIG. 4A) where upper and lower jaws 102, 104 are closer together, and in an open position or configuration (FIG. 4B) where upper and lower jaws 102, 104 are farther apart. Device 100 can include an actuating jaw lever 120 and a locking mechanism 130 such as a ratchet mechanism post 131. As shown here, a locking mechanism can include a locking spring 132, a gear 134, and a pivot 136. The gear 134 is configured to engage a pawl 138. In FIG. 4B, the actuating jaw lever 120 is raised or actuated, the actuating jaw spring 142 is expanded, the locking spring 132 is compressed, the pawl 138 is positioned lower (relative to the position shown in FIG. 4A), the gear 134 of the locking or ratchet mechanism 130 is not engaged with the pawl 138, and the locking (ratchet) mechanism 130 is released. In FIG. 4A, the locking (ratchet) mechanism 130 is engaged.

Hence, the device 100 can have a ratchet mechanism 130 that includes an elongated post 131 that rotates about a pivot 136. The post or elongated body 131 can include serrations, teeth, gears, or the like, that couple with the device actuating jaw 104 (or with the actuating jaw extension 104A). For example, the rotation or pivoting of the post 131 about the pivot 136 can allow engagement and disengagement of the post teeth 134 with the pawl 138 of the actuating jaw 104 (or of the lower jaw extension 104A), so as to enable the jaws 102, 104 to be locked in position relative to one another in configurations having varying distances between the jaws, so as to enable the adjustment of the subject distance between the jaws. The ratchet mechanism post 131 can be spring loaded (e.g. via locking spring 132) to be biased or naturally rotate into locking position and to also allow rotation into a disengaged position.

In some embodiments, a device actuation jaw 104 can be loaded with a compression spring 142 along the direction of linear motion. In some embodiments, a device handle or lever 120 can be spring loaded (e.g. via spring 142) into the open position allowing a manual compression of the actuating jaw (e.g. by actuation of lever 120 in the direction indicated by arrow B) into the closed position. The handle or lever 120 can be coupled with a lift mechanism to actuate the actuating jaw 104 from and open to closed position. Hence, as shown here, when a proximal portion 133 of the post 131 is moved as indicated by arrow A, spring 132 is compressed, teeth 134 become disengaged from pawl 138, and spring 142 can then force lower jaw 104 in a downward direction (e.g. by pressing downward on a lower jaw extension 104A). Movement of the lever 120 in the direction indicated by arrow B can cause the lower jaw 104 to move upward toward the upper jaw 102, and can cause compression of spring 142.

Figure 5C:
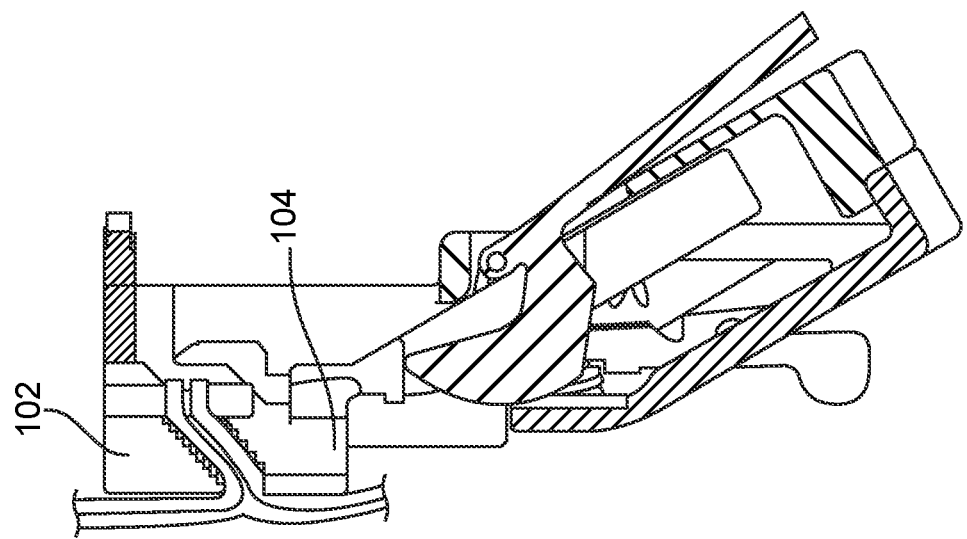
Figure 5D:
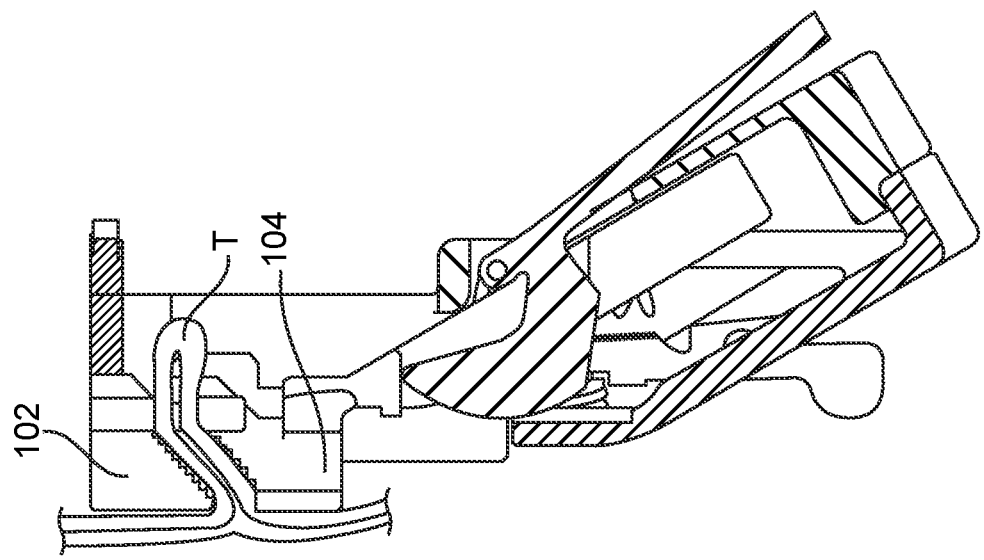

FIGS. 5A and 5B provide additional views of device 100 in an open position or configuration (FIG. 5A) where upper and lower jaws 102, 104 are farther apart, and in a closed position or configuration (FIG. 5B) where upper and lower jaws 102, 104 are closer together. As shown here, device 100 includes an actuating jaw lever pivot 122 (about which actuating jaw lever 120 can pivot relative to the base 180) and an actuating jaw guide post 124. Hence, in contrast to a device that includes a movable handle and a fixed handle moving in linear motion, embodiments of the present invention encompass devices having a pivot feature 122 to provide the lever 120 actuating the adjustable jaw 104. Advantageously, exemplary blepharoplasty system devices use a pivot rotation (e.g. about pivot 122) to establish linear adjustment between the two surface contacting jaws, as well as a pivot rotation (e.g. about pivot 136 shown in FIG. FIG. 4A) to establish releasable locking between the two jaws. As shown in FIG. 5C, a portion of eyelid tissue T can be clamped between the upper and lower jaws 102, 104. As shown in FIG. 5D, eyelid tissue can then be removed.

Figure 6E:
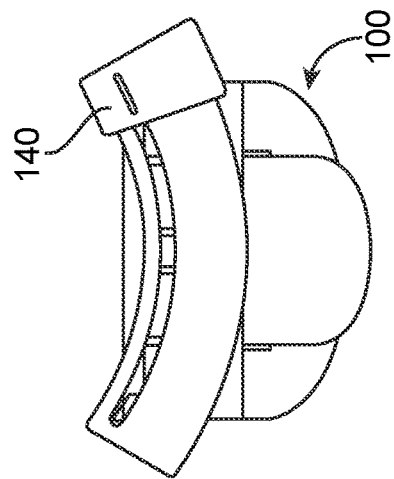
FIGS. 6A to 6I depict aspects of an excess skin removal and wound closure device, in accordance with some embodiments of the present invention.
Figure 6F:
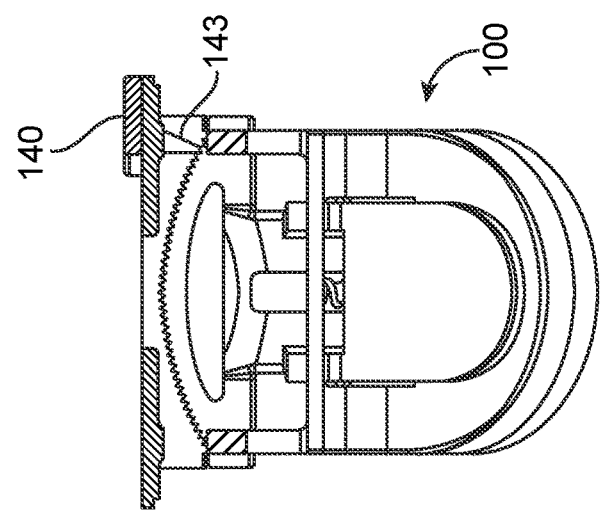
Figure 6C:
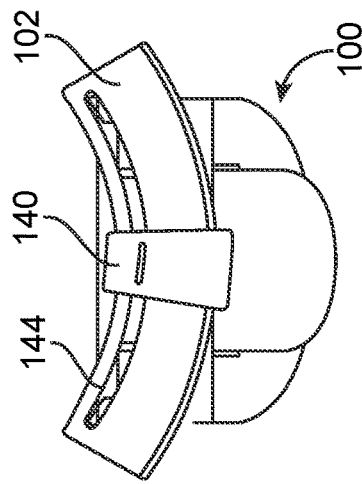
Figure 6D:
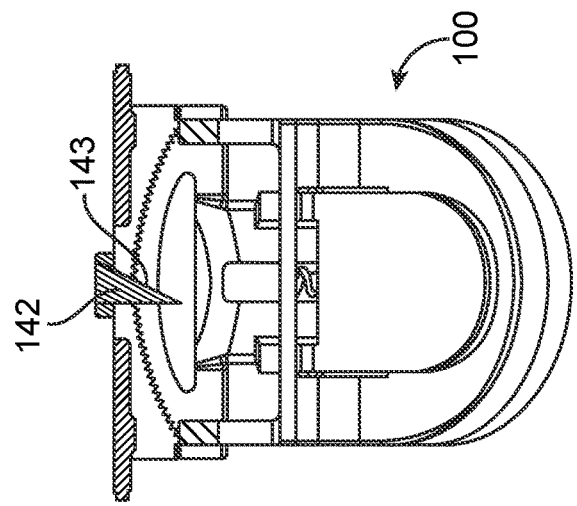
Figure 6A:
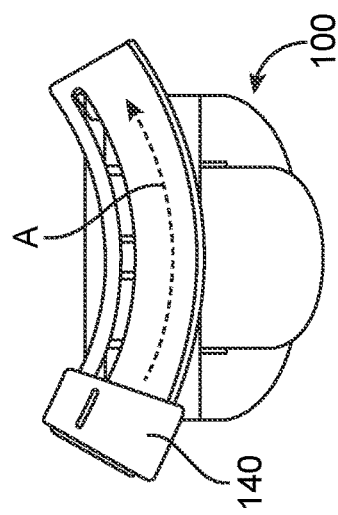
Figure 6B:
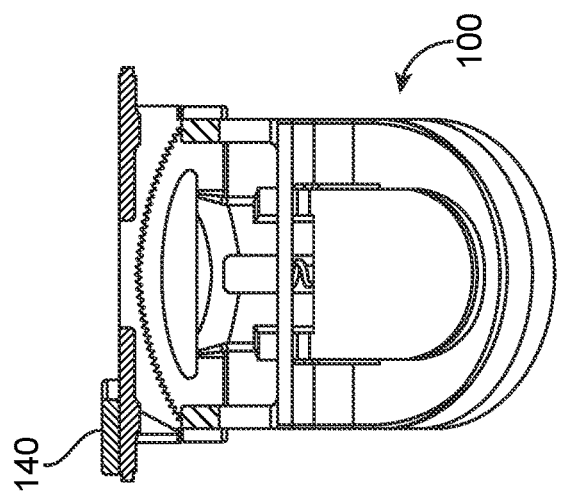
Figure 6I:
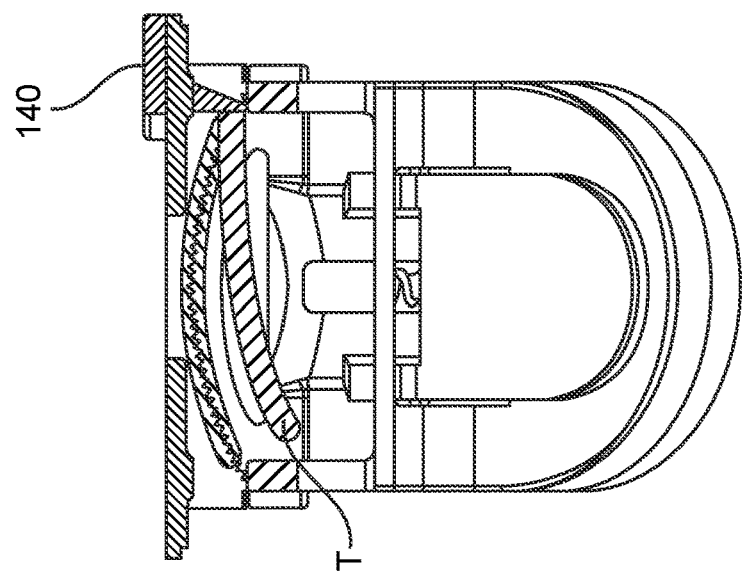
Figure 6H:
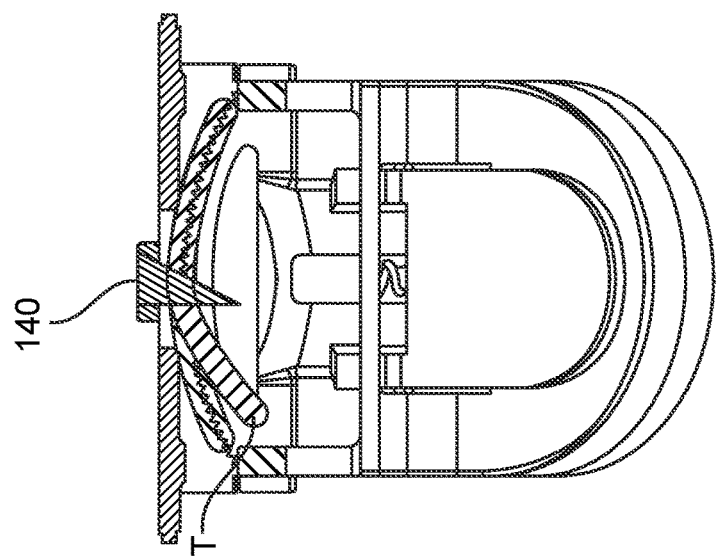
Figure 6G:
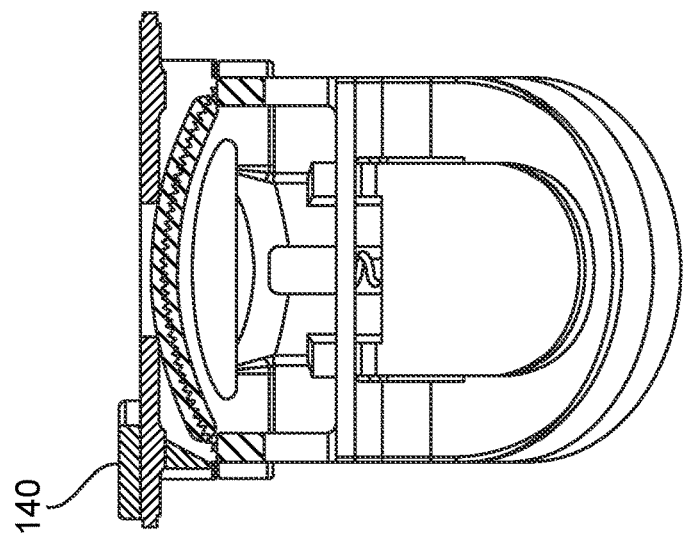

FIGS. 6A to 6F provide various illustrations of a blepharoplasty device 100, according to embodiments of the present invention. As shown here, device 100 can include a cutting mechanism 140 having a cutting member or blade 142. The cutting member 142 has a cutting edge 143. The cutting mechanism 140 can be a sliding cutting mechanism, and can slide from one side of the device to the opposite side of the device, for example in the direction indicated by arrow A. As shown here, blade 142 can slide along or within blade guide 144 of upper jaw 102. FIGS. 6G to 6I illustrate how eyelid tissue T can be removed via operation of the cutting mechanism.

Figures 7A, 7B:
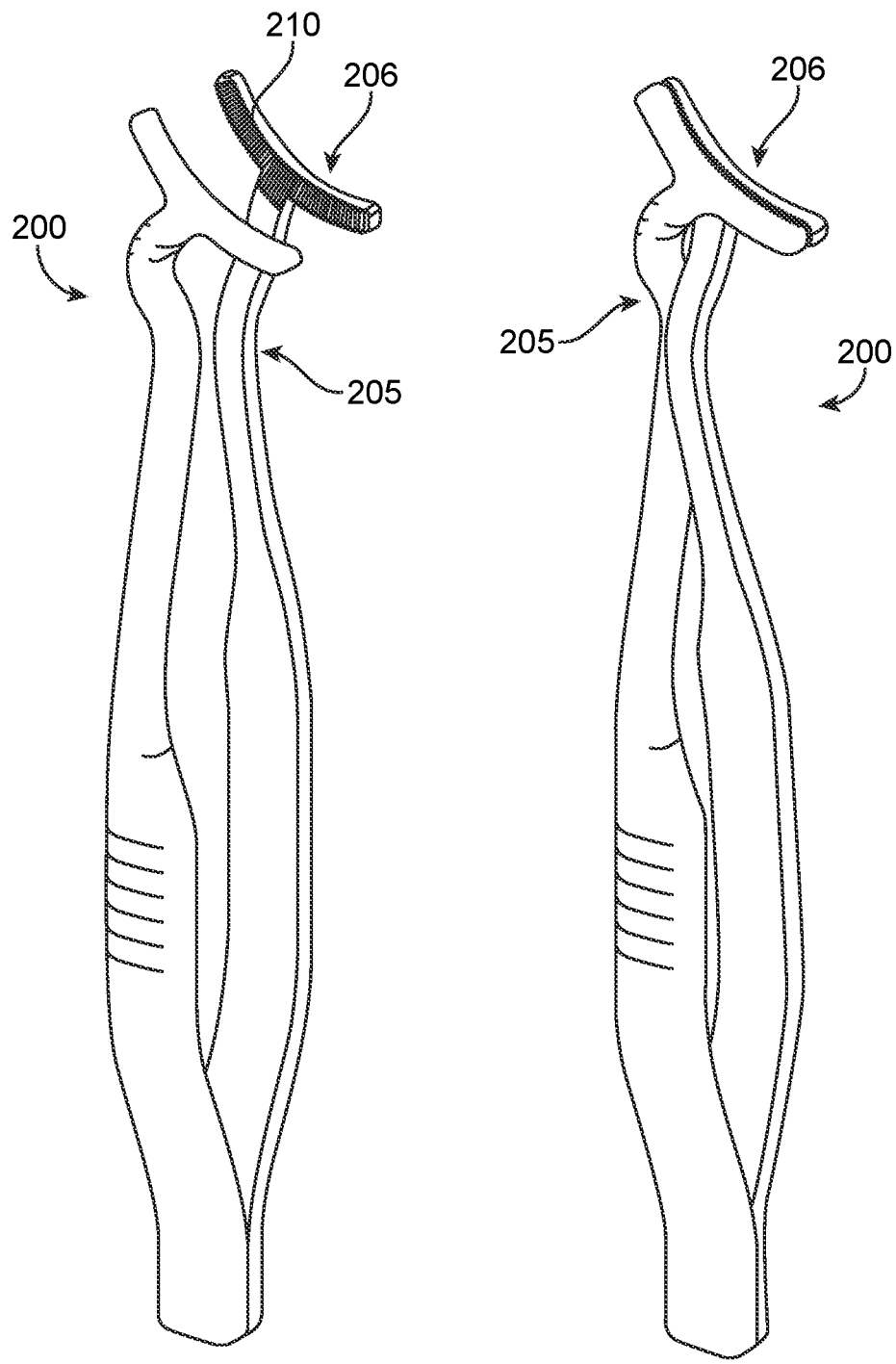
FIGS. 7A and 7B depict aspects of a grasping tool, in accordance with some embodiments of the present invention.

FIGS. 7A and 7B illustrate aspects of a grasping tool or forceps 200 in an open position or configuration (FIG. 7A) and in a closed position or configuration (FIG. 7B). The grasping tool 200 can include skin contact serrations 210.

An elongated end (e.g. 205) of the forceps or grasping tool can be of various curvatures, widths, and lengths. In some embodiments, a distal end (e.g. 206) of the forceps or grasping tool can be curved to conform to the intended tissue subject for manipulation, and relatedly, a distal end of a grasping tool can include any of the curve features disclosed herein which correspond to jaw members of a device (e.g. as discussed with reference to FIGS. 1A, 1B, 16A, and 16B). The present disclosure further contemplates the inclusion of various lengths and widths for a tissue contacting distal end (e.g. 206) which can be configured to grasp surface areas of tissue. It is understood that the grasping tool or forceps 2200 depicted in FIGS. 22A and 22B and/or the grasping tool or forceps 2200A depicted in FIGS. 22C and 22D can similarly have an elongated end of various curvatures, widths, and lengths. Likewise, a distal end of the forceps or grasping tool (2200 or 2200A) can be curved to conform to the intended tissue subject for manipulation, and relatedly, a distal end of a grasping tool can include any of the curve features disclosed herein which correspond to jaw members of a device (e.g. as discussed with reference to FIGS. 1A, 1B, 16A, and 16B). The present disclosure further contemplates the inclusion of various lengths and widths for a tissue contacting distal end of a forceps or grasping tool 2200 or 2200A which can be configured to grasp surface areas of tissue.

With returning reference to FIGS. 7A and 7B, the grasping tool can be used (e.g. by a surgeon or operator) to position patient tissue relative to a blepharoplasty device. For example, when a blepharoplasty device is in the open position, a portion of patient tissue can be positioned between the upper and lower jaws thereof. The grasping tool 200 can be used to facilitate the movement of the tissue into the space between the upper and lower jaws. For example, the grasping tool 200 can grip upper eyelid tissue of a patient and pull it away from the patient and into the space between the upper and lower jaws.

Embodiments of the present invention can include kits having a skin grasping tool (e.g. forceps 200), a local topical anesthetic agent, an incision bonding agent, a marker, and an iodine swab. The grasping tool (e.g. forceps 200) can have an elongated body divided into two serrated tissue contacting surfaces at the distal end. The contacting surfaces can be curved comparable to the anteroposterior curve of the eyelid skin tissue. The distal end contacting surfaces can be adjustable between two distances, an open position (e.g. 8 mm) and a closed position (e.g. 0 mm). In some embodiments, the distance between surfaces is adjustable manually with compression. The serrations on the contacting surfaces can provide a shear force between the eyelid skin tissue and grasping tool allowing positioning of skin tissue through the jaws of the device component. The elongated body can include a section with a reduced width to fit through the open jaws of the device component. In operation, the skin grasping tool (e.g. forceps 200) can fit through the device from the anterior direction and expands and compresses to grab or grasp and pull the tissue through.

Exemplary treatment procedures can include marking the area of the eyelid tissue desired for removal with a marker and providing a local anesthetic to temporarily anesthetize the surgical area. After the surgical area is fully anesthetized, the surgical site can be disinfected with an iodine swab. The grasping tool can enter through the open jaws of the device, compress into the closed position, and grab or grasp the marked eyelid skin tissue area, then pull the tissue through the open jaws of the device. The device can then close fully clamping the tissue, cutting blood flow. A cutting mechanism can then be used to remove the eyelid skin tissue. After tissue is removed, an incision bonding agent can be applied on the incision, sealing it and allowing it to heal.

Hence, embodiments of the present invention encompass kits having of a skin grasping tool, a marker, a local topical anesthetic, an iodine swab, and an incision bonding agent to fully complete a blepharoplasty procedure method.

Figure 8A:
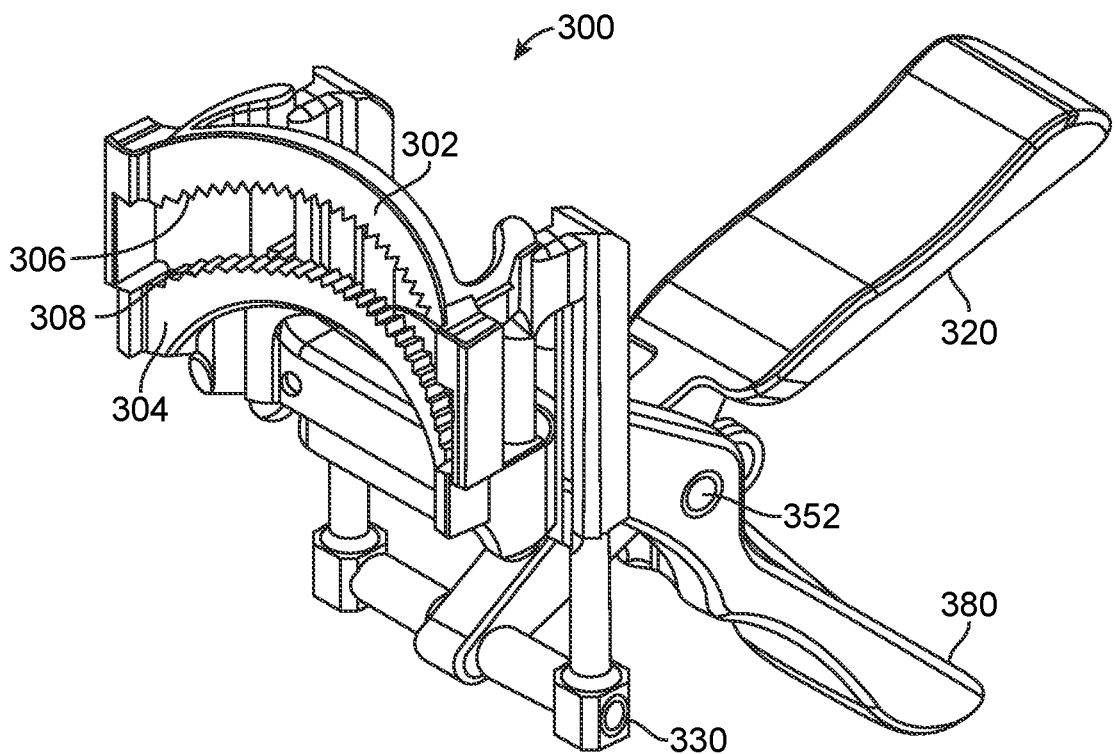
FIGS. 8A and 8B depict aspects of an excess skin removal and wound closure device, in accordance with some embodiments of the present invention.
Figure 8B:
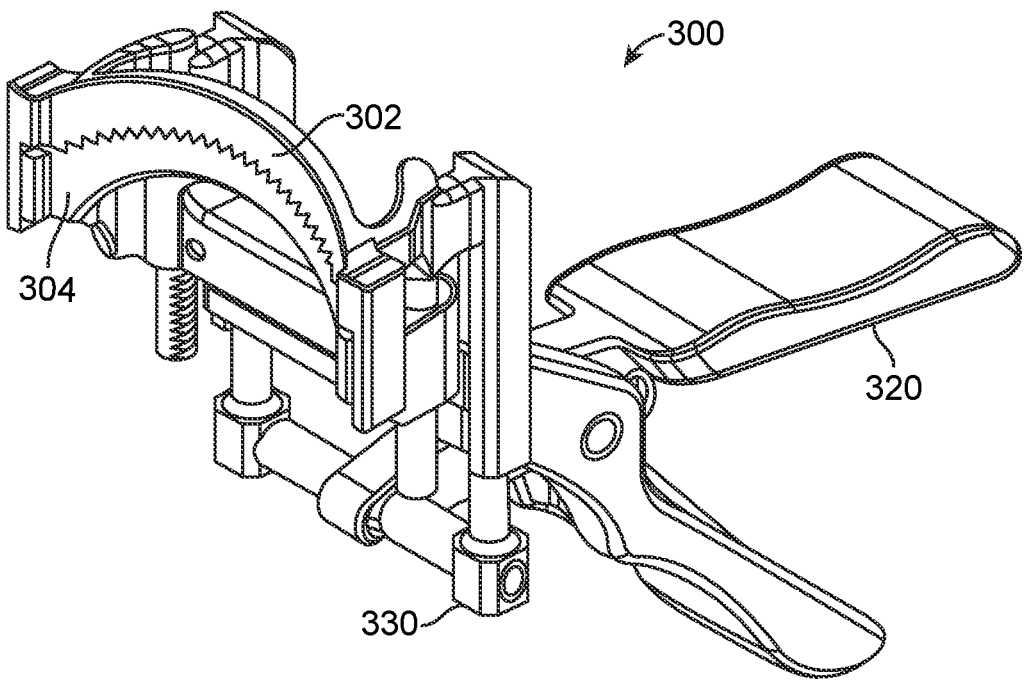

FIGS. 8A and 8B illustrate an embodiment of a blepharoplasty device 300 that is configured to capture eyelid tissue to facilitate tissue excision from a portion of an eyelid. Device 300 is a tissue gripping device (e.g. a clamp) comprised of a pair of elongated jaw members 302, 304 operatively connected together so that they can be moved relative to one another between an open position (FIG. 8A) and a closed position (FIG. 8B). Upper jaw members 302 and lower jaw member 304 can be curved to follow a contour of the eyelid area to produce a desired incision shape.

In some embodiments, the upper jaw member would be considered the superior jaw member and the lower jaw member would be considered the inferior jaw member because of their relative positions with respect to the head and feet. For purposes of simplicity, the terms "upper' and "lower" are used herein to refer to the superior and inferior members, although it should be understood that "upper" and "lower" do not imply any positional relationship aside from the anatomical reference points of the body.

Upper jaw member 302 has a first tissue contacting surface 306 and lower jaw member 304 has a second tissue contacting surface 308. First and second tissue contacting surfaces 306, 308 generally face one another in an opposing manner so that when eyelid tissue is positioned between upper and lower jaw members 302, 304, first and second tissue contacting surfaces 306, 308 can move towards one another to capture and secure the eyelid tissue between the first and second tissue contacting surfaces 306, 308.

When upper jaw member 302 and lower jaw member 304 are in the open position (FIG. 8A), first and second tissue contacting surfaces 306, 308 are separated by a distance to form an opening or space that is large enough to receive eyelid tissue. As upper and lower jaw members 302, 304 move together to the closed position (FIG. 8B), the distance between first and second contacting surfaces 306, 308 is reduced to a smaller distance. With this smaller distance, the opening or space between first and second tissue contacting surfaces 306, 308 is small enough to capture and secure any eyelid tissue positioned between first and second tissue contacting surfaces 306, 308. As shown here, first and second tissue contacting surfaces 306, 308 may include serrated jaw features or serrations. Hence, embodiments of the present invention encompass devices having jaws with serrations to allow the clamped skin to crush onto itself creating a desired site for cutting. In some embodiments, the upper jaw member 302 can be referred to as a fixed jaw, and the lower jaw member 304 can be referred to as an actuating jaw.

First and second tissue contacting surfaces 306, 308 are configured to grip and hold eyelid tissue that is positioned between the opposing first and second tissue contacting surfaces 306, 308. Device 300 can be used in combination with a grasping tool. Device 300 may also include a jaw actuation handle 320 and a jaw actuation lift 330.

Embodiments of the present invention provide unique blepharoplasty system, including related devices, kits, and methods for the removal of excess eyelid skin tissue and the sealing of incised skin. Exemplary devices can include two curved serrated skin contacting jaws with one jaw fixed (e.g. upper member 302) and one jaw actuating (e.g. lower member 304) between a closed and open position in which the open position allows eyelid skin tissue to protrude in between the jaws and the closed position clamps the skin tissue restricting blood flow to the eyelid skin tissue. An actuating mechanism can include a lever or handle with a pivot rotation adjusting the linear position of the actuating jaw relative to the fixed jaw. For example, as depicted in FIG. 8A, jaw actuation handle 320 can pivot about handle pivot 352 relative to base 380. In some cases, an actuating jaw or handle can be coupled to a ratchet mechanism allowing the distance between jaws to be locked in various distances between fully opened (e.g. 8 mm) and fully closed (e.g. 0 mm). A ratchet mechanism can include a mechanism to release the coupling of the ratchet mechanism allowing the re-adjustment of the actuating jaw. In some embodiments, a device can include or be configured to operate in association with a cutting attachment, and the cutting attachment can include an actuating mechanism to cut the clamped eyelid skin tissue.

In some embodiments, a blepharoplasty device may include silicone coated jaws (e.g. jaws 302, 304). The presence of silicone can operate to reduce the ability for the adhesive to adhere to the jaws of the device, allowing the ability to seal the incision with adhesive while the skin is clamped within the jaws.

Figure 9A:
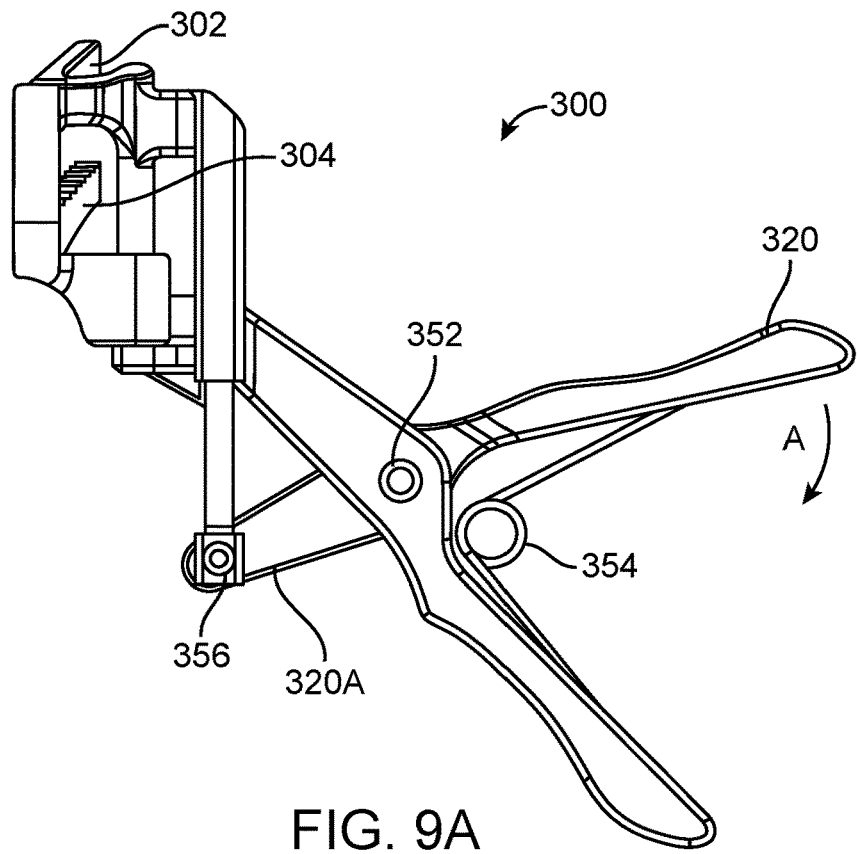
FIGS. 9A and 9B depict aspects of an excess skin removal and wound closure device, in accordance with some embodiments of the present invention.
Figure 9B:
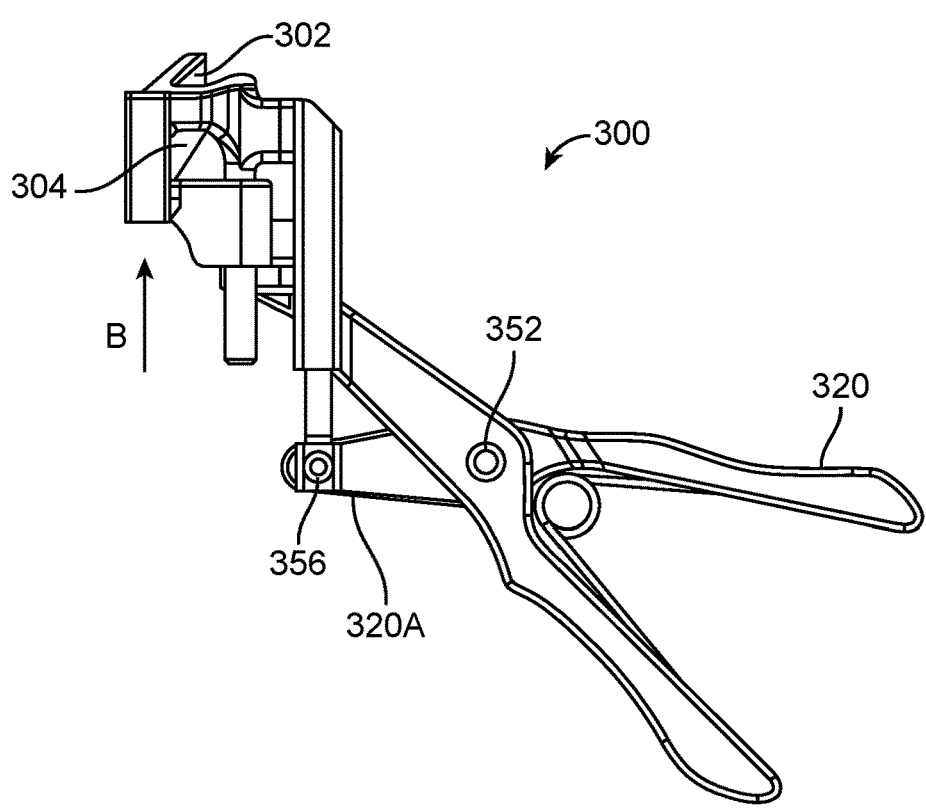

FIGS. 9A and 9B provide additional views of device 300 in an open position or configuration (FIG. 9A) where upper and lower jaws are farther apart, and in a closed position or configuration (FIG. 9B) where upper and lower jaws are closer together. As shown here, device 300 includes a handle pivot 352, a jaw actuation handle spring 354, and an actuation lift pivot 356. Hence, in contrast to a device that includes a movable handle and a fixed handle moving in linear motion, embodiments of the present invention encompass devices having a pivot feature to provide the lever actuating the adjustable jaw. Advantageously, exemplary blepharoplasty system devices use a pivot rotation to establish linear adjustment between the two surface contacting jaws. For example, as shown here, handle 320 can be pressed in a pivoting downward direction as indicated by arrow A, resulting in an upward movement of handle extension 320A, which in turn causes linear upward movement of lower jaw 304 relative to upper jaw 302, as indicated by arrow B.

Figure 10A:
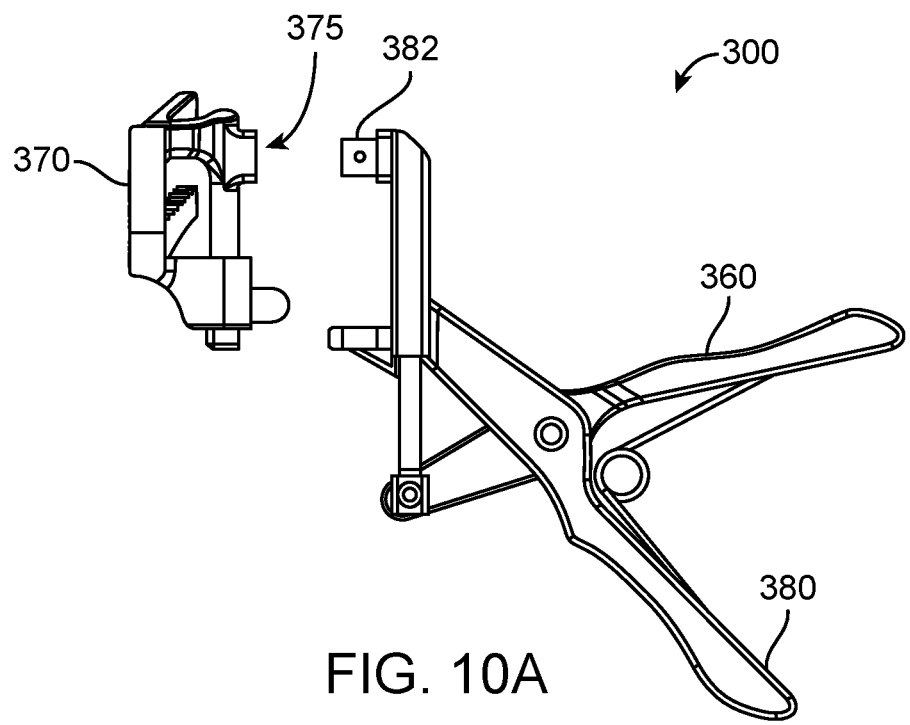
FIGS. 10A and 10B depict aspects of an excess skin removal and wound closure device with a removable jaw mechanism, in accordance with some embodiments of the present invention.
Figure 10B:
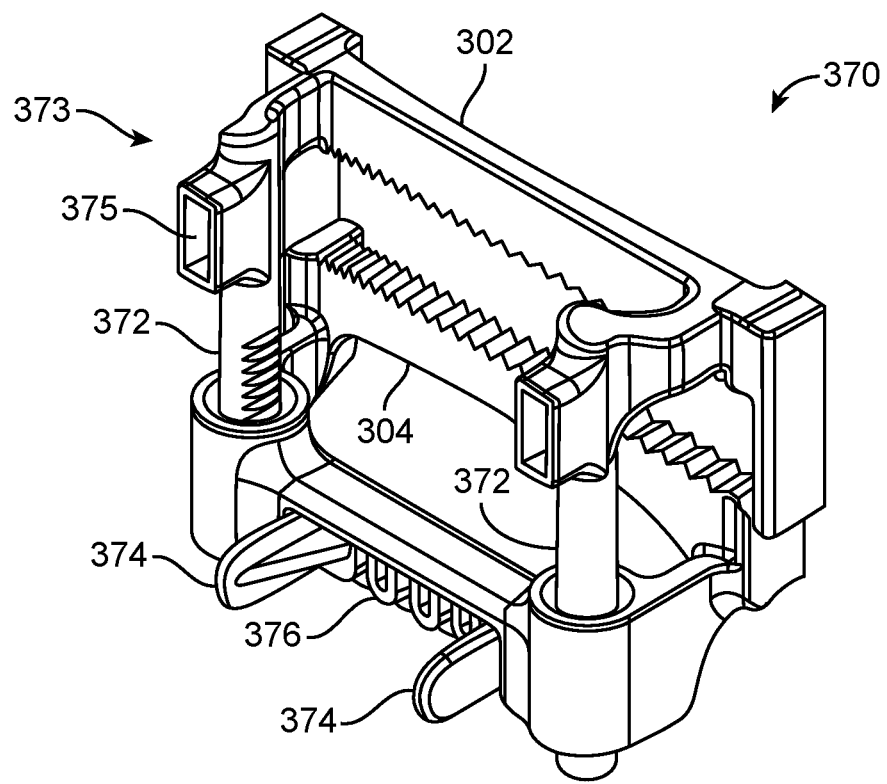

FIG. 10A illustrates aspects of an embodiment of a blepharoplasty device 300 according to embodiments of the present invention. As shown here, blepharoplasty device 300 includes a handle mechanism 360 and a removable jaw mechanism 370. FIG. 10B illustrates aspects of a removable jaw mechanism 370, according to some embodiments. Removable jaw mechanism 370 can include actuating jaw guide locking posts 372, locking mechanism compression tabs 374, and a locking (ratchet) mechanism 376. The locking (ratchet) mechanism 376 can operate to control the distance between the upper jaw member 302 and lower jaw member 304 when locked. Embodiments of the present invention encompass devices having a ratchet mechanism to allow actuating jaw locking at various distances and allow adjustment of the skin tissue subject for removal. In some embodiments, posts 372 can constitute or be part of a support assembly 373 of the first jaw member 302. In some embodiments, support assembly 373 includes a recess 375 and the base 380 includes a tab 382. The recess 375 and the tab 382 can provide a releasably engageable coupling between the first jaw member and the base. In some cases, support assembly 373 can include multiple recesses, and base 380 can include multiple tabs.

Figure 11A:
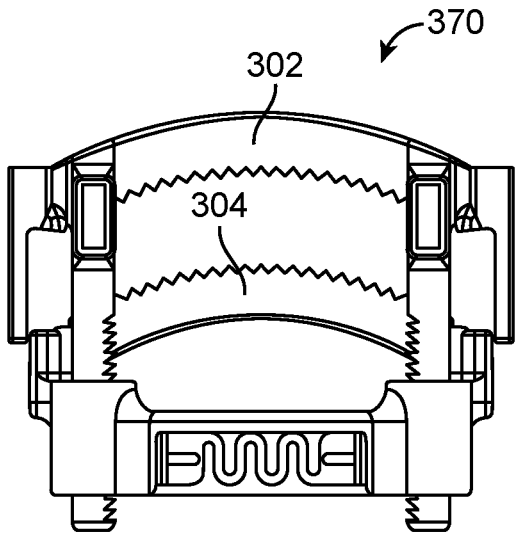
FIGS. 11A to 11D depict aspects of a removable jaw mechanism, in accordance with some embodiments of the present invention.
Figure 11B:
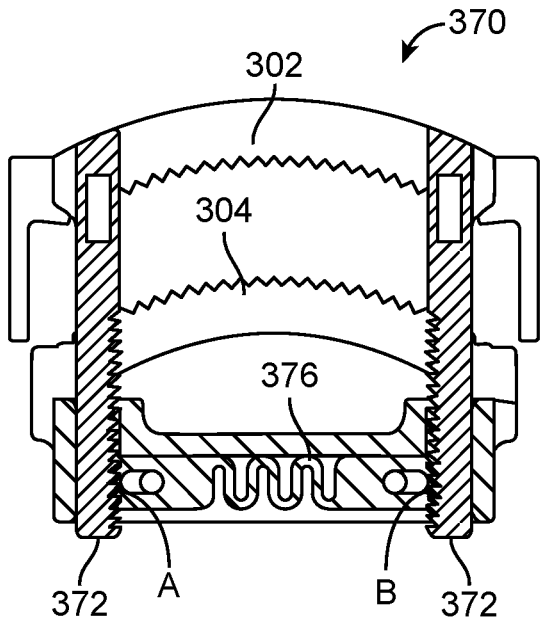
Figure 11C:
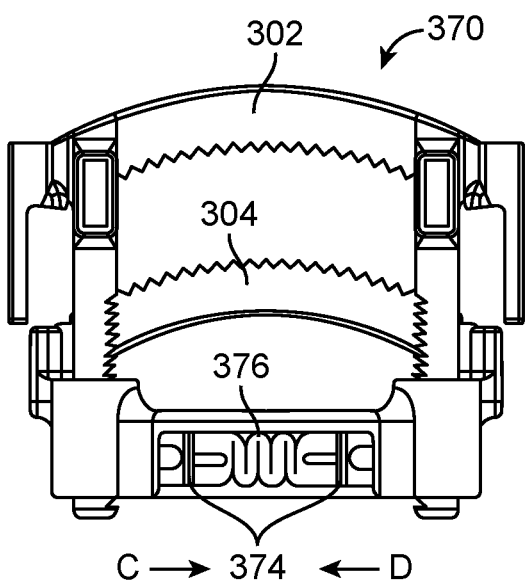
Figure 11D:
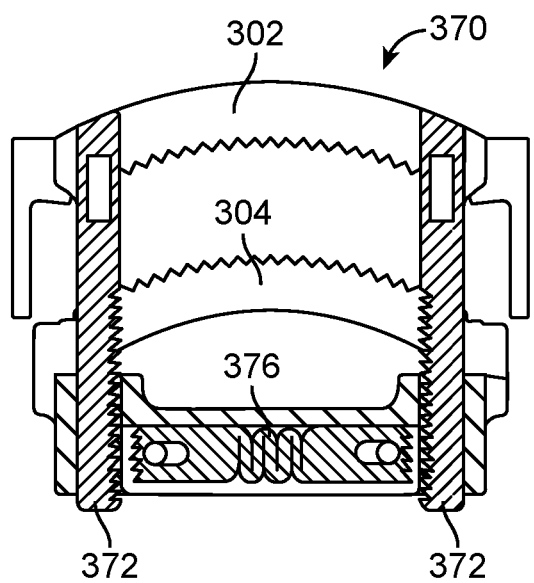

FIGS. 11A to 11D depict aspects of a removable jaw mechanism 370, according to some embodiments. FIG. 11B illustrates an engagement between the actuating jaw guide locking posts 372 and the locking (ratchet) mechanism 376. For example, teeth of the locking (ratchet) mechanism 376 can engage teeth of the actuating jaw guide locking posts 372 at engagement zones A and B. As shown in FIG. 11C, the locking mechanism compression tabs 374 can be brought closer together toward one another (e.g. in directions indicated by arrows C and D), so as to compress the locking (ratchet) mechanism 376 from each side, thereby disengaging the locking (ratchet) mechanism 376 form the actuating jaw guide locking posts 372, as shown in FIG. 11D. Hence, FIGS. 11A and 11B depict a configuration where the locking mechanism is engaged, and FIGS. 11C and 11D depict a configuration where the locking mechanism is released or disengaged. When the locking mechanism is released or disengaged, it is possible to adjust or readjust the positioning of the upper jaw member 302 relative to the lower jaw member 304, as the upper jaw member is in fixed relationship relative to the actuating jaw guide locking posts 372.

Hence, embodiments of the present invention encompass devices having a ratchet mechanism which can include serrations, teeth, gears, or the like on each end that couples with posts of the device actuating jaw. An exemplary ratchet or locking mechanism 376 can include a series of cuts or a serpentine section providing flexure that allows the entire elongated body to compress, uncoupling the ratchet to the actuating jaw allowing adjustment of the tissue desired for removal.

Figure 12A:
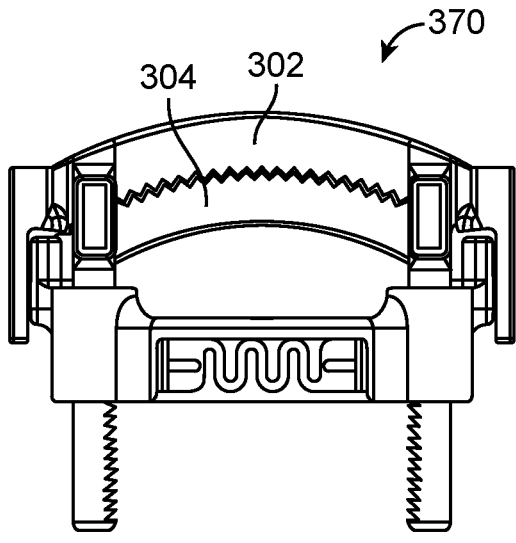
FIGS. 12A to 12E depict aspects of a removable jaw mechanism, in accordance with some embodiments of the present invention.
Figure 12B:
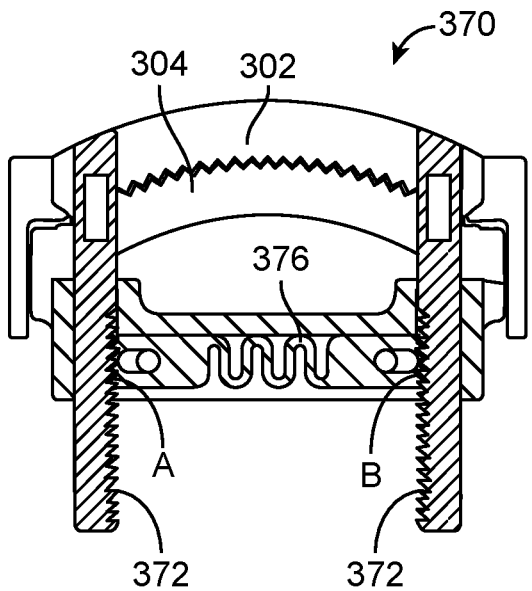
Figure 12C:
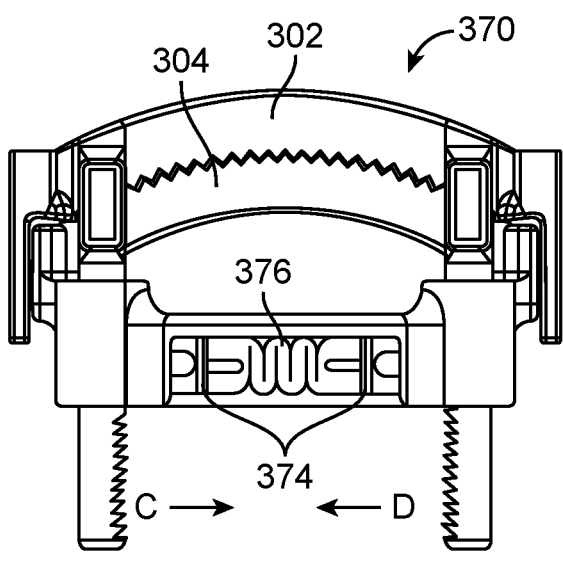
Figure 12D:
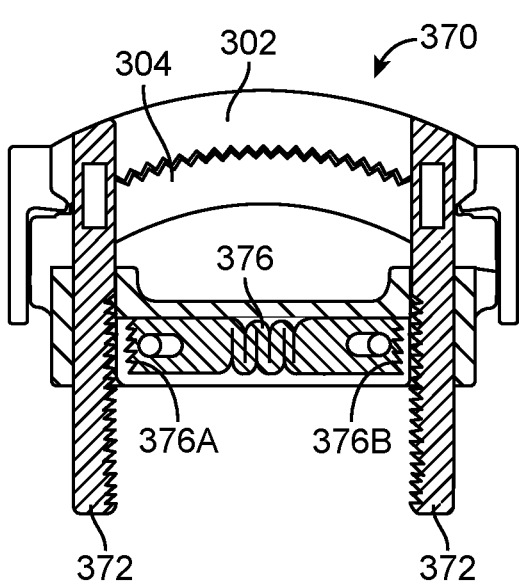

FIGS. 12A to 12D depict aspects of a removable jaw mechanism 370, according to some embodiments. FIG. 12B illustrates an engagement between the actuating jaw guide locking posts 372 and the locking (ratchet) mechanism 376. For example, teeth of the locking (ratchet) mechanism 376 can engage teeth of the actuating jaw guide locking posts 372 at engagement zones A and B. As shown in FIG. 12C, the locking mechanism compression tabs 374 can be brought closer together toward one another (e.g. in directions indicated by arrows C and D), so as to compress the locking (ratchet) mechanism 376 from each side, thereby disengaging the locking (ratchet) mechanism 376 form the actuating jaw guide locking posts 372, as shown in FIG. 12D. Hence, FIGS. 12A and 12B depict a configuration where the locking mechanism is engaged, and FIGS. 12C and 12D depict a configuration where the locking mechanism is released or disengaged. When the locking mechanism is released or disengaged, it is possible to adjust or readjust the positioning of the upper jaw member 302 relative to the lower jaw member 304, as the upper jaw member is in fixed relationship relative to the actuating jaw guide locking posts 372.

Figure 12E:
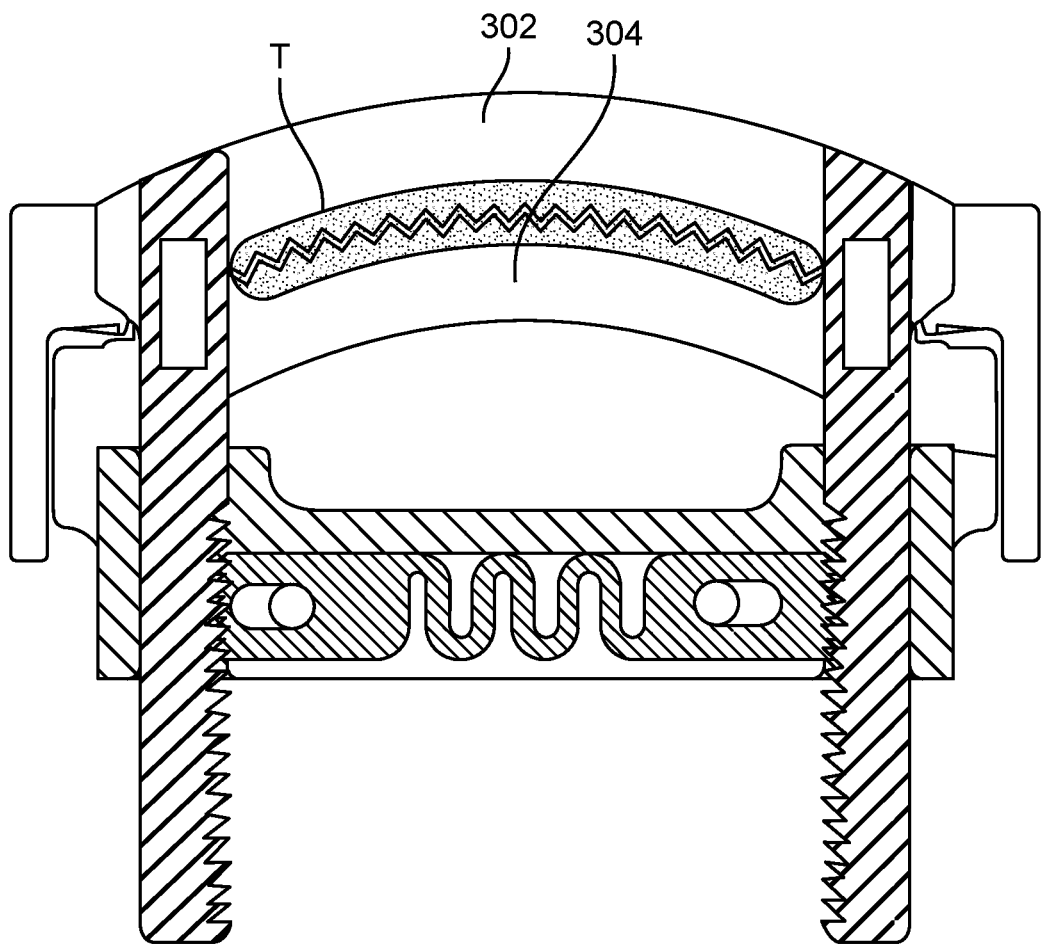

Hence, embodiments of the present invention provide devices having a ratchet mechanism that include an elongated body 376 with teeth 376A, 376B on each end that couples with posts 372 of the device actuating jaw 304. The ratchet mechanism can have a series of cuts or a serpentine section providing flexure that allows the entire elongated body to compress, uncoupling the ratchet to the actuating jaw. The ratchet mechanism can have posts 372 extending perpendicular to the elongated body 376, allowing manual disengagement of the ratchet mechanism to the actuating jaw and actuation from closed to open position. FIG. 12E depicts eyelid tissue T disposed between the upper jaw 302 and the lower jaw 304.

Figure 13A:
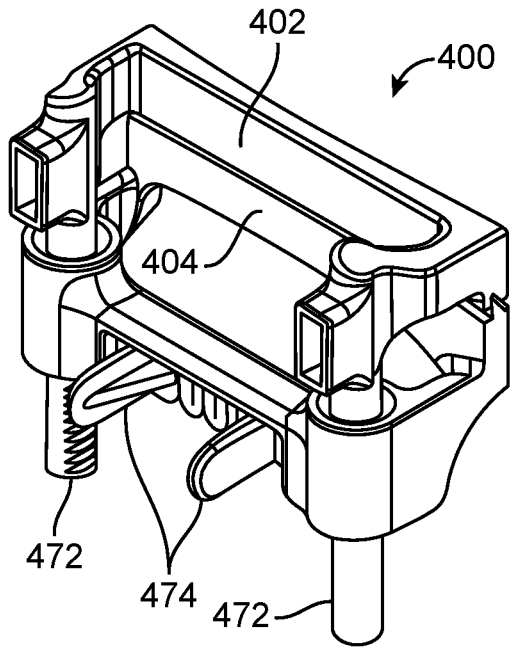
FIGS. 13A to 13D depict aspects of an attachable cutting mechanism, in accordance with some embodiments of the present invention.
Figure 13B:
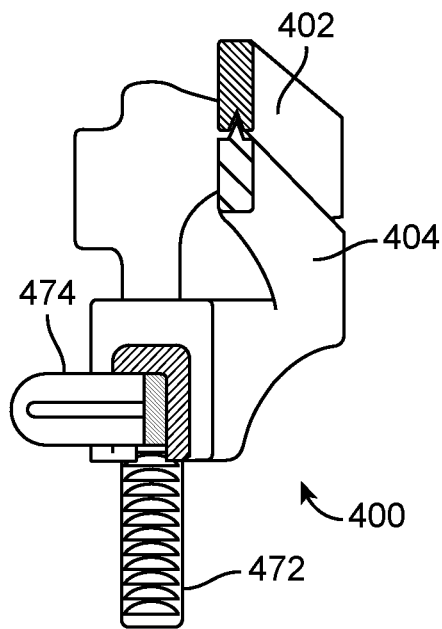
Figure 13C:
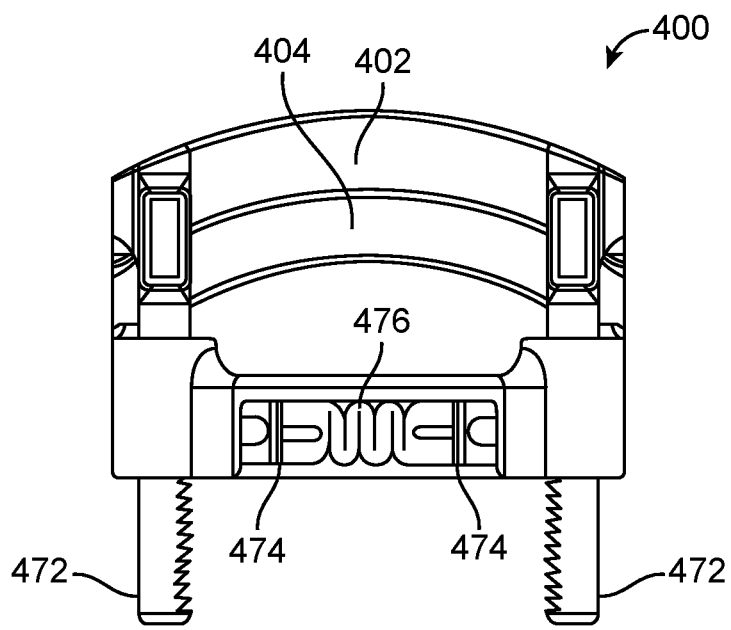
Figure 13D:
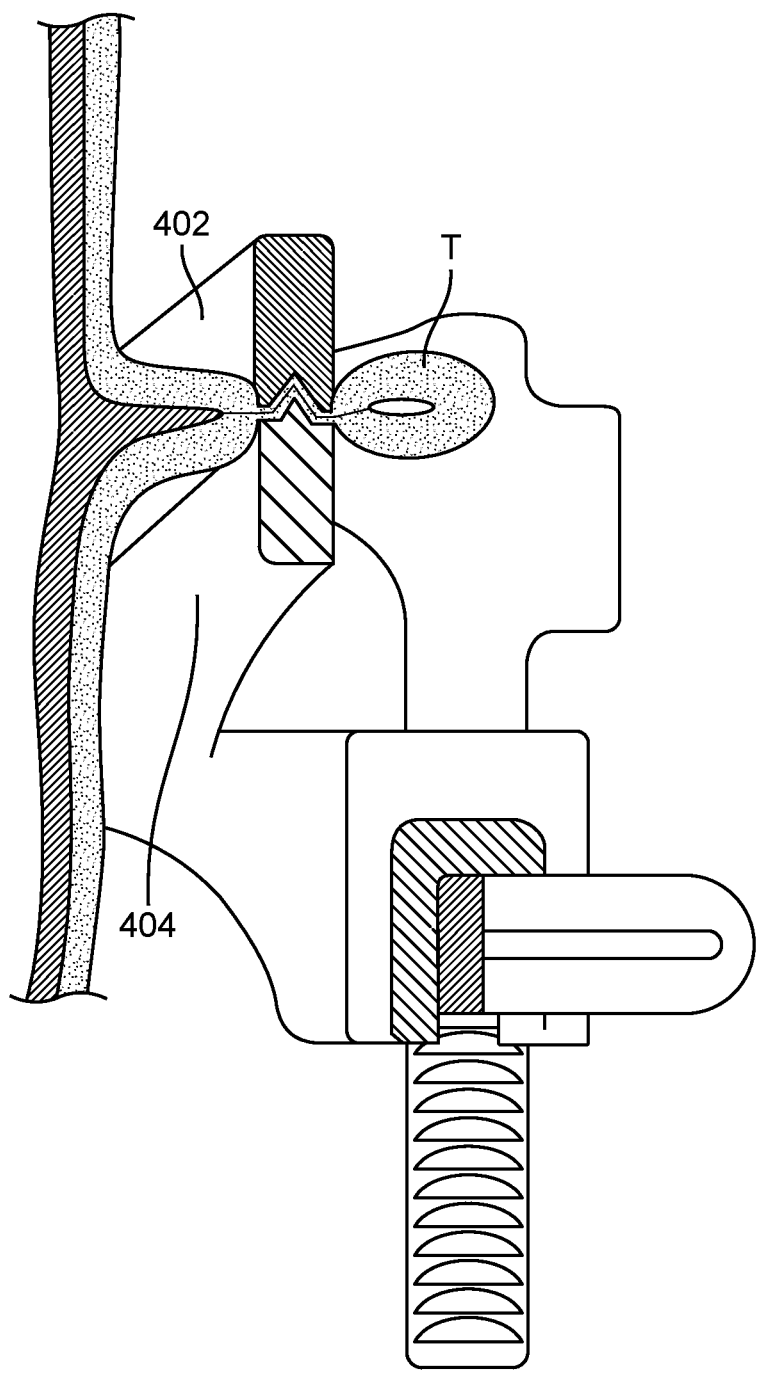

FIGS. 13A to 13C depict aspects of an attachable cutting mechanism 400, according to embodiments of the present invention. The attachable cutting mechanism 400 can include actuating cutting guide locking posts 472, locking mechanism compression tabs 474, and a locking (ratchet) mechanism 476. The locking (ratchet) mechanism 476 can operate to control the distance between the upper cutting member 402 and lower cutting member 404 when locked. According to some embodiments, the locking mechanism components of the attachable cutting mechanism 400 operate in a manner similar to the locking mechanism components of the removable jaw mechanism 370. FIGS. 13A to 13C depict the attachable cutting mechanism 400 in a closed or chop cutting position or configuration. FIG. 13D depicts eyelid tissue T disposed between the upper cutting member 402 and the lower cutting member 404. In some embodiments, a blepharoplasty device may include silicone coated jaws (e.g. jaws 402, 404). The presence of silicone can operate to reduce the ability for the jaws to adhere to skin, allowing the ability to seal the incision with adhesive while the skin is clamped within the jaws.

Figure 14D:
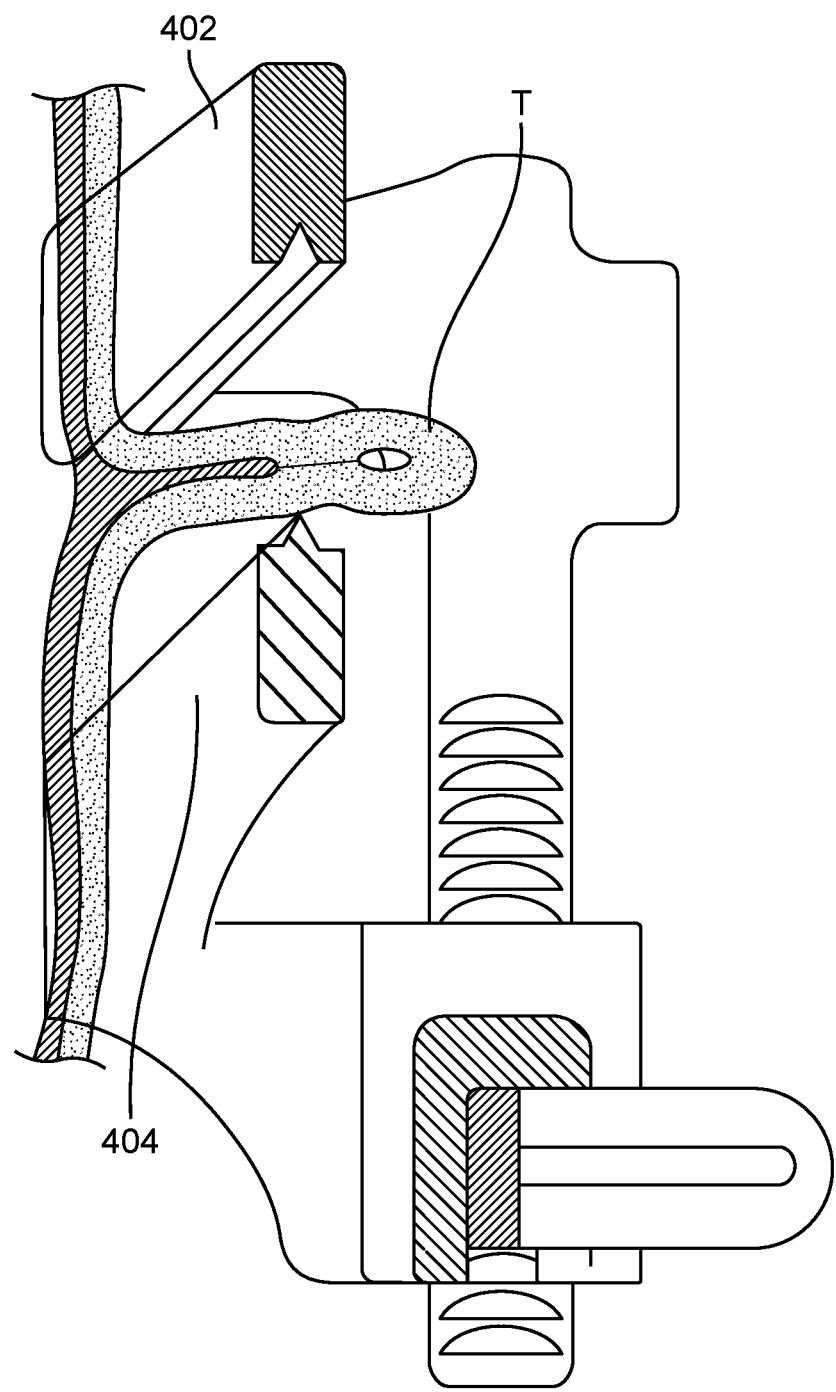

FIGS. 14A to 14C depict aspects of an attachable cutting mechanism 400, according to embodiments of the present invention. The attachable cutting mechanism 400 can include actuating cutting guide locking posts 472, locking mechanism compression tabs 474, and a locking (ratchet) mechanism 476. The locking (ratchet) mechanism 476 can operate to control the distance between the upper cutting member 402 and lower cutting member 404 when locked. Upper cutting member 402 includes a cutting blade pocket 403, and lower cutting member 404 includes a cutting blade 404 that is configured to engage the pocket 403 to perform cutting of tissue when the tissue is disposed therebetween. In some cases, the pocket is disposed on the lower member 404 and the blade is disposed on the upper member 402. According to some embodiments, the locking mechanism components of the attachable cutting mechanism 400 operate in a manner similar to the locking mechanism components of the removable jaw mechanism 370. FIGS. 14A to 14C depict the attachable cutting mechanism 400 in an open position or configuration. FIG. 14D depicts eyelid tissue T disposed between the upper cutting member 402 and the lower cutting member 404. Hence, such a cutting attachment 400 can actuate in the superior-inferior directions through skin tissue, for the removal of a desired amount of skin tissue. According to some embodiments, use of removable jaw mechanism 370 shown in FIGS. 13A to 13C can be combined with use of a cutting attachment 400 shown in FIGS. 14A to 14C. In some embodiments, the skin response under the clamp force and the serrations can operate to keep the skin portion (which is desired for removal) to remain protruding after releasing the clamp (e.g. after jaws 302, 304 shown in FIG. 12E are separated). A cutting mechanism can then be attached to a handle mechanism and/or base, and surround the protruded tissue and actuate to remove it (e.g. as shown in FIG. 13D).

Blepharoplasty device embodiments disclosed herein can be provided in various widths, allowing alternatives to varying patient anatomies. In some instances, a cutting mechanism can be pre-assembled within the device clamping the skin (e.g. as depicted in FIGS. 1A and 1B, and FIGS. 6A to 6F). In some instances, a cutting mechanism can be provided as an assembly that is separate from the device clamping the skin (e.g. as depicted in FIGS. 14A to 14C).

In some instances, a cutting mechanism can be a sliding cutting mechanism that actuates in the medial-lateral direction perpendicular to the clamped tissue, for example as depicted in FIGS. 6A to 6F. Hence, embodiments of the present invention encompass devices having a cutting mechanism that can cut skin sliding in the medial-lateral direction. In some cases, a cutting mechanism can actuate in the superior-inferior direction perpendicular to the to the skin tissue surface, for example as depicted in FIGS. 14A to 14C. Hence, embodiments of the present invention encompass devices that can chop skin with a cutting mechanism moving perpendicular to the clamped skin site.

Figure 15B:
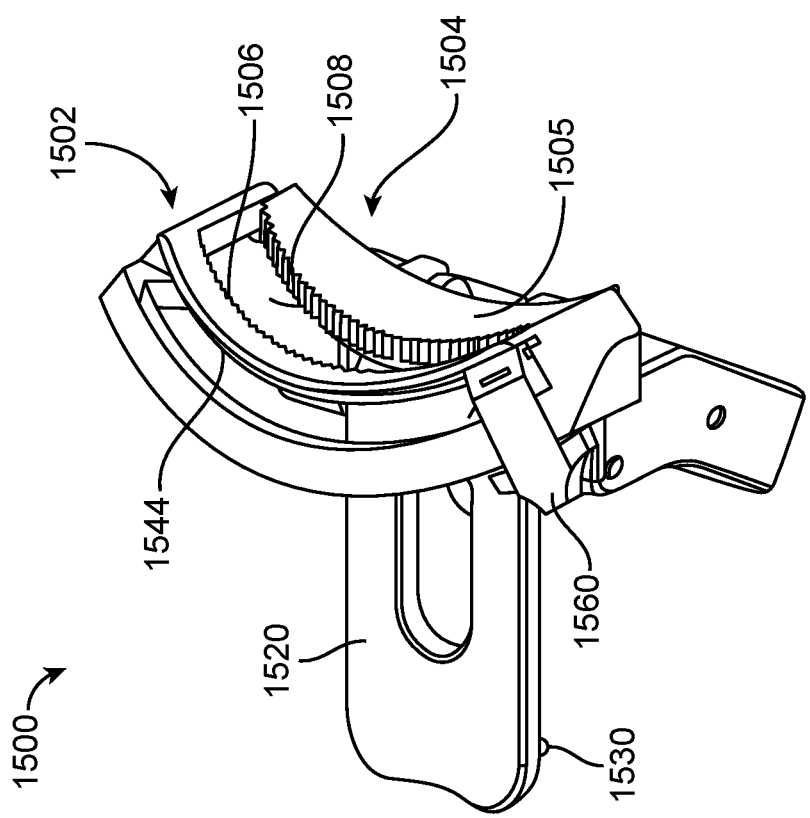
FIGS. 15A and 15B depict aspects of an excess skin removal and wound closure device, in accordance with some embodiments of the present invention.
Figure 15A:
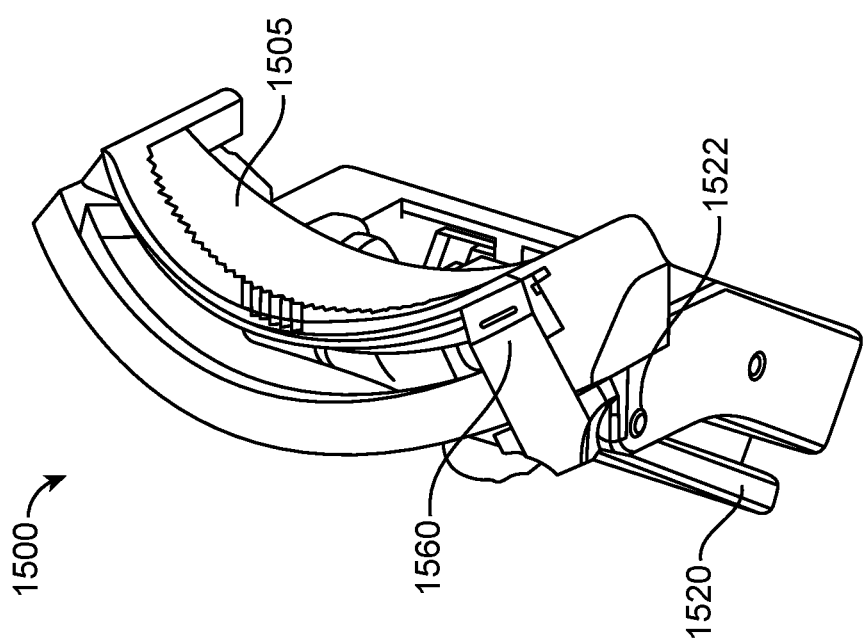

FIGS. 15A and 15B illustrate an embodiment of a blepharoplasty device 1500 that is configured to capture eyelid tissue to facilitate tissue excision from a portion of an eyelid. Device 1500 is a tissue gripping device (e.g. a clamp) comprised of a pair of elongated jaw members 1502, 1504 operatively connected together so that they can be moved relative to one another between an open position (FIG. 15B) and a closed position (FIG. 15A). Upper jaw members 1502 and lower jaw member 1504 can be curved to follow a contour of the eyelid area to produce a desired incision shape. In some embodiments, a jaw member can have a superoinferior curve of radius 1⅜ inches and an anteroposterior curve of radius 1⅝ inches to establish contour. In some cases, the contour created is established from patient anatomy imaging.

In some embodiments, the upper jaw member would be considered the superior jaw member and the lower jaw member would be considered the inferior jaw member because of their relative positions with respect to the head and feet. For purposes of simplicity, the terms "upper" and "lower" are used herein to refer to the superior and inferior members, although it should be understood that "upper" and "lower" do not imply any positional relationship aside from the anatomical reference points of the body.

Upper jaw member 1502 has a first tissue contacting surface 1506 and lower jaw member 1504 has a second tissue contacting surface 1508. First and second tissue contacting surfaces 1506, 1508 generally face one another in an opposing manner so that when eyelid tissue is positioned between upper and lower jaw members 1502, 1504, first and second tissue contacting surfaces 1506, 1508 can move towards one another to capture and secure the eyelid tissue between the first and second tissue contacting surfaces 1506, 1508. In some embodiments, first and second tissue contacting surfaces 1506, 1508 have respective serrated portions that face toward one another.

When upper jaw member 1502 and lower jaw member 1504 are in the open position (FIG. 15B), first and second tissue contacting surfaces 1506, 1508 are separated by a distance to form an opening or space that is large enough to receive eyelid tissue. As upper and lower jaw members 1502, 1504 move together to the closed position (FIG. 15A), the distance between first and second contacting surfaces 1506, 1508 is reduced to a smaller distance. With this smaller distance, the opening or space between first and second tissue contacting surfaces 1506, 1508 is small enough to capture and secure any eyelid tissue positioned between first and second tissue contacting surfaces 1506, 1508.

First and second tissue contacting surfaces 1506, 1508 are configured to grip and hold eyelid tissue that is positioned between the opposing first and second tissue contacting surfaces 1506, 1508. Device 1500 also includes a cutting member or cutting mechanism slider 1560. A cutting mechanism slider 1560 can include or be coupled with a cutting blade (not shown) and the blade can be moved along and/or within a blade guide 1544. As shown here, blade guide 1544 can be a curved slit, track, or edge along the upper jaw 1502. Advantageously, as further discussed herein, such a cutting mechanism can actuate in the medial lateral directions through skin tissue, for the removal of a desired amount of skin tissue. In some embodiments, lower jaw member 1504 may be referred to as an actuating jaw. As shown in FIGS. 15A and 15B, actuating jaw 1504 may include a tissue contacting side 1505. In some cases, tissue contacting side 1505 may be referred to as an eyelid contacting surface or an eyelid contacting contoured surface. Device 1500 may also include an actuating jaw lever or lever mechanism 1520, and a locking mechanism 1530 such as a lever latch lock mechanism or ratchet mechanism post. Embodiments of the present invention encompass devices having a ratchet mechanism to allow actuating jaw locking at various distances and allow adjustment of the skin tissue subject for removal. In some cases, a locking mechanism can be attached to an actuating handle component of the device.

Hence, embodiments of the present invention provide unique blepharoplasty system, including related devices, kits, and methods for the removal of eyelid skin tissue and the sealing of incised skin. Exemplary devices can include two curved serrated skin contacting jaws with one jaw fixed (e.g. upper member 1502) and one jaw actuating (e.g. lower member 1504), whereby the configuration of the device can be alternated between a closed position (e.g. FIG. 15A) and an open position (e.g. FIG. 15B), in which the open position allows eyelid skin tissue to protrude in between the jaws and the closed position clamps the skin tissue restricting blood flow to the eyelid skin tissue. An actuating mechanism can include a lever 1520 with a pivot 1522, whereby actuation of the actuating jaw lever 1520 about the pivot 1522 enables an adjusting of the linear position of the actuating jaw 1504 relative to the fixed jaw 1502 (e.g. between open configuration shown in FIG. 15B where lever 1520 is in an upward position, and closed configuration shown in FIG. 15A where lever is in a downward position).

In some cases, a fixed jaw 1502 (or a component in fixed relationship with the fixed jaw) can be releasably coupled with a ratchet mechanism 1530 allowing the distance between jaws 1502, 1504 to be locked in various distances between fully opened (e.g. 8 mm) and fully closed (e.g. 0 mm). A ratchet mechanism 1530 can include a mechanism to release the coupling of the ratchet mechanism allowing the re-adjustment of the actuating jaw 1504. As further discussed elsewhere herein, in some embodiments, a device can include or be configured to operate in association with a cutting attachment, and the cutting attachment can include an actuating mechanism to cut the clamped eyelid skin tissue.

In some embodiments, a blepharoplasty device may include silicone coated jaws (e.g. jaws 1502, 1504). The presence of silicone can operate to reduce the ability for the adhesive to adhere to the jaws of the device, allowing the ability to seal the incision with adhesive while the skin is clamped within the jaws.

FIGS. 16A and 16B provide additional views of device 1500 in an open position or configuration (FIG. 16B) where upper and lower jaws 1502, 1504 are farther apart, and in a closed position or configuration (FIG. 16A) where upper and lower jaws 1502, 1504 are closer together. Alternating between the open and closed configurations can involve linear movement of the lower (e.g. actuating) jaw 1504 relative to the upper (e.g. fixed) jaw 1502, as indicate by arrow A. First and second contacting surfaces 1506, 1508 can have serrated edges. Hence, embodiments of the present invention encompass devices having jaws with serrations to allow the clamped skin to crush onto itself creating a desired site for cutting. Serrations can be interlocking allowing the skin tissue to deform to the point that the desired amount of skin for removal remains protruded and the skin remains crushed after the clamp has released.

Figure 17A:
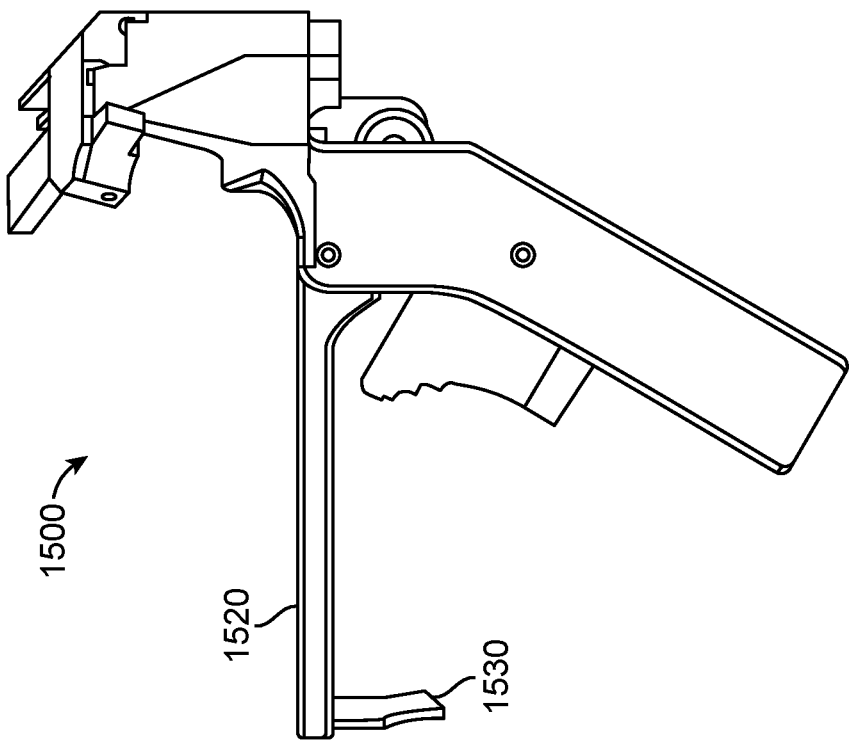
FIGS. 17A and 17B depict aspects of an excess skin removal and wound closure device, in accordance with some embodiments of the present invention.
Figure 17B:
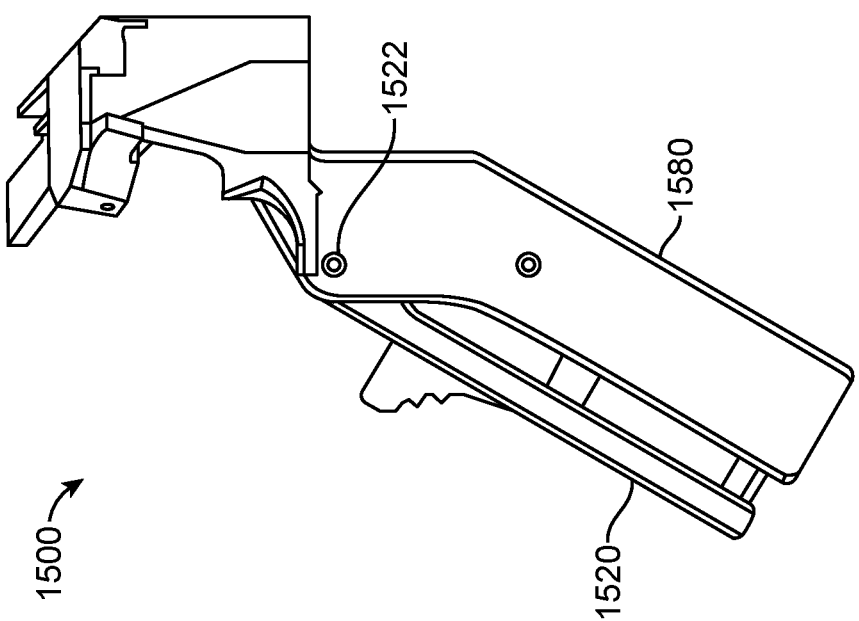

FIGS. 17A and 17B provide additional views of device 1500 in a closed position or configuration (FIG. 17A) where upper and lower jaws are closer together, and in an open position or configuration (FIG. 17B) where upper and lower jaws are farther apart. Device 1500 can include an actuating jaw lever 1520 and a locking mechanism 1530 such as a lever latch lock mechanism or ratchet mechanism post. Pivot 1522 enables actuating jaw lever 1520 to pivot relative to a base 1580 of the device 1500.

Figure 18B:
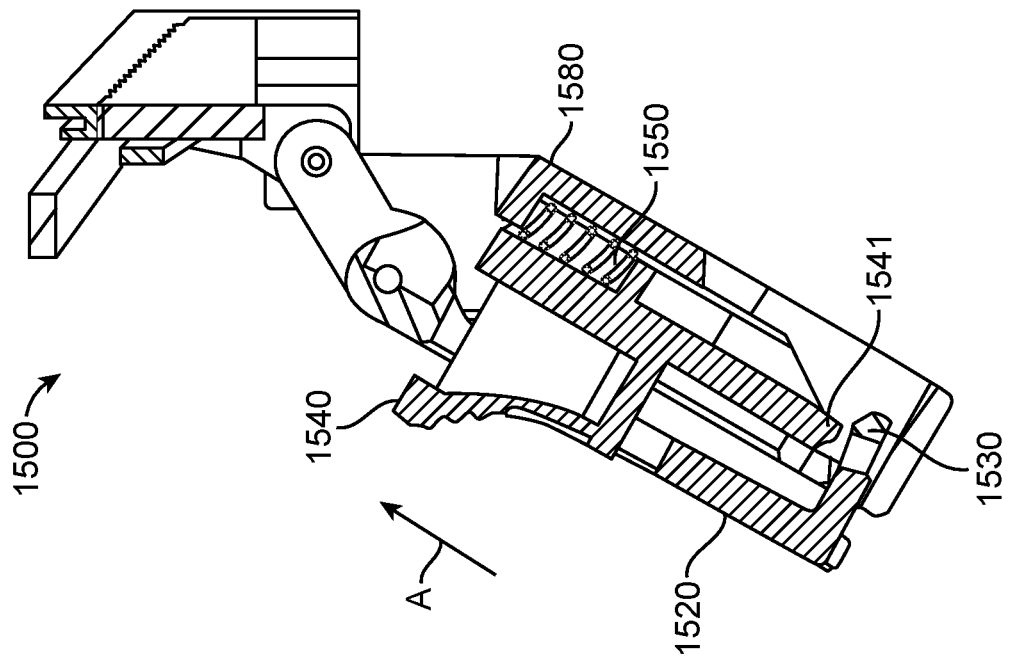
FIGS. 18A to 18C depict aspects of an excess skin removal and wound closure device, in accordance with some embodiments of the present invention.
Figure 18A:
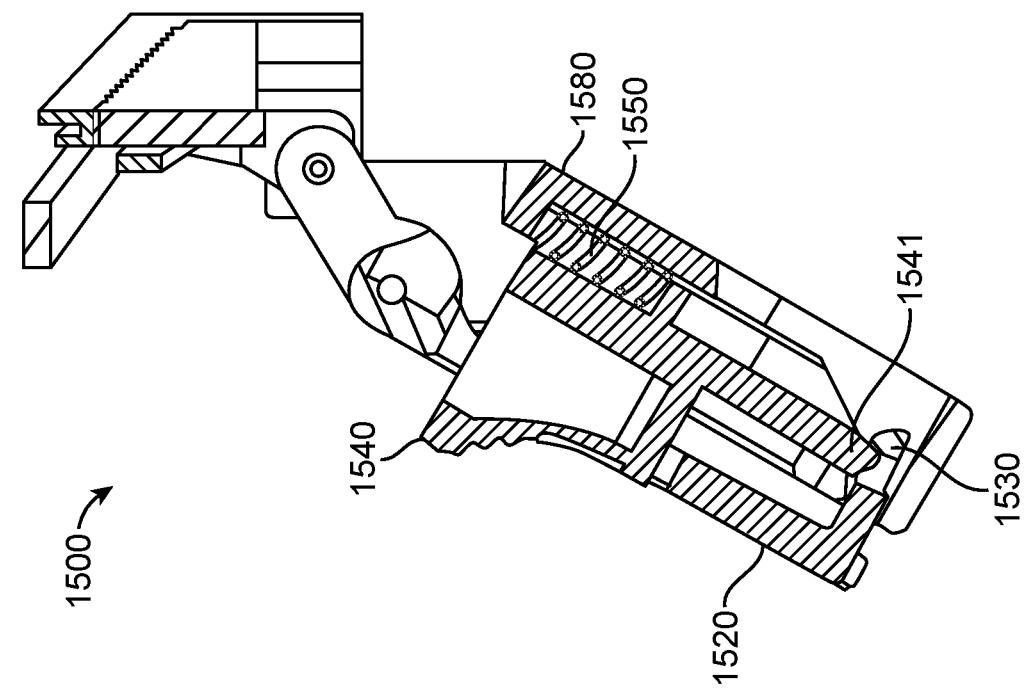

FIGS. 18A and 18B provide additional views of device 1500 in a closed position or configuration where upper and lower jaws are closer together or in contact with one another. Device 1500 can include an actuating jaw lever 1520 having a locking mechanism 1530 such as a lever latch lock mechanism or ratchet mechanism post. Device 1500 can also include a latch mechanism 1540 having a latch mechanism engagement component 1541. As shown in FIG. 18A, the latch mechanism engagement component 1541 can engage the locking mechanism 1530, such that the latch mechanism 1540 and the locking mechanism 1530 are in a locked configuration relative to one another.

Figure 18C:
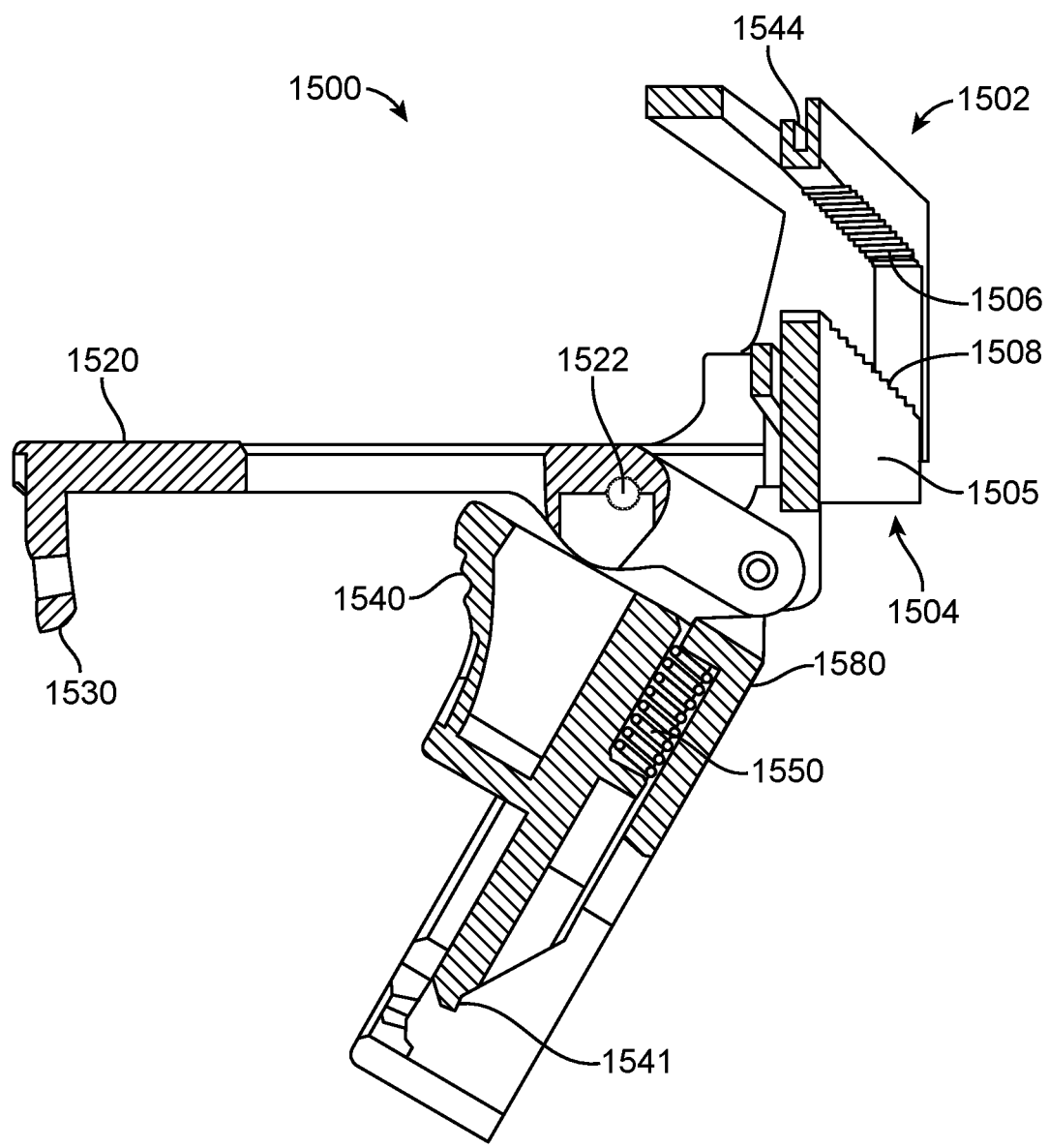

As shown in FIG. 18B, the latch mechanism engagement component 1541 can be disengaged from the locking mechanism 1530, such that the latch mechanism 1540 and the locking mechanism 1530 are not in a locked configuration relative to one another. This can be accomplished by moving the latch mechanism in a latch release motion or distal direction, as indicated by arrow A, which can consequently operate to compress a latch spring 1550 (e.g. compressing spring 1550 between base 1580 and latch mechanism 1540. FIG. 18C provides a cross-section view of device 1500 in an open configuration. As shown, here, actuating jaw lever 1520 can pivot relative to handle 1580 via actuating jaw lever pivot 1522.

Figure 19B:
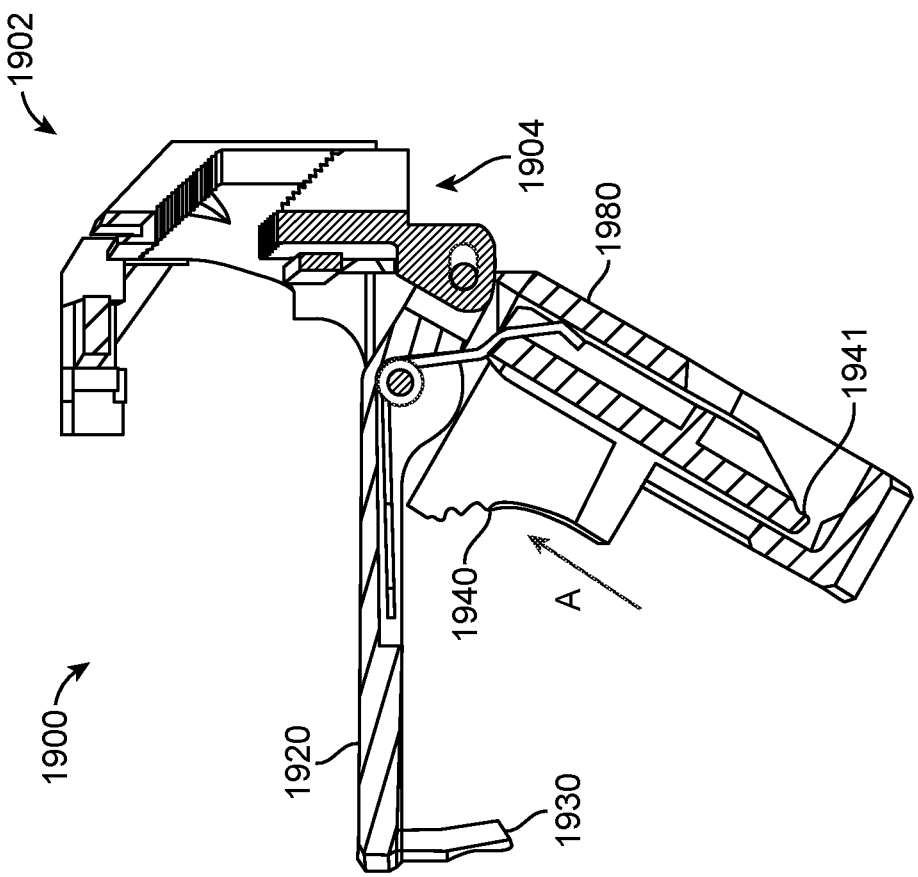
FIGS. 19A and 19B depict aspects of an excess skin removal and wound closure device, in accordance with some embodiments of the present invention.
Figure 19A:
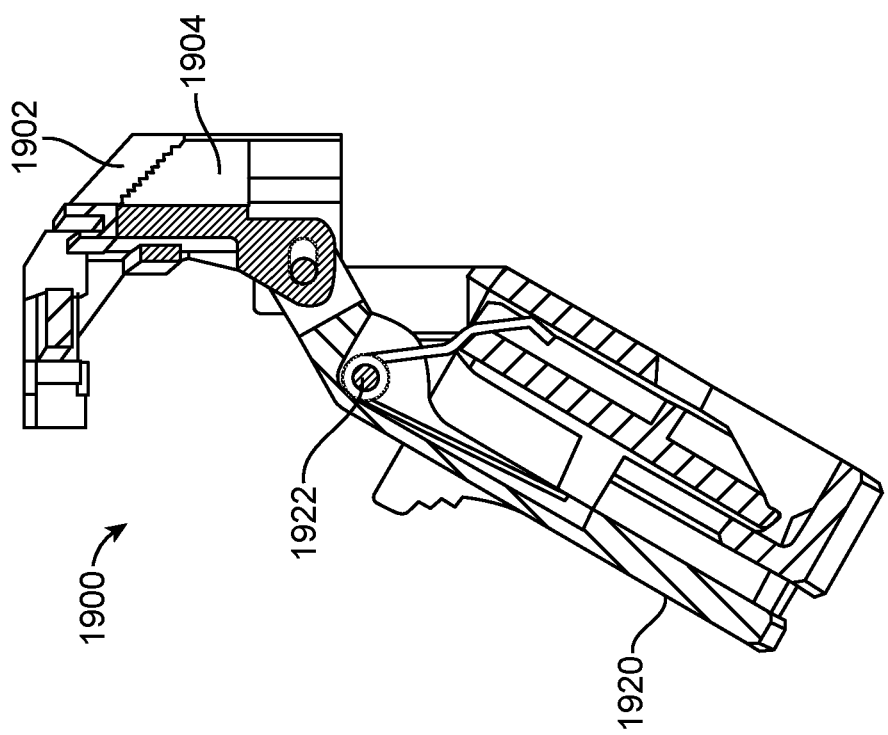

FIGS. 19A and 19B provide cross-section views of a device 1900 in a closed position or configuration (FIG. 19A) where upper and lower jaws 1902, 1904 are closer together or in contact with one another and in an open configuration (FIG. 18B) where upper and lower jaws 1902, 1904 are farther apart from one another. Device 1900 can include an actuating jaw lever 1920 having a locking mechanism 1930 such as a lever latch lock mechanism or ratchet mechanism post. Device 1500 can also include a latch mechanism 1540 having a latch mechanism engagement component 1541. The latch mechanism engagement component 1941 can engage the locking mechanism 1930, such that the latch mechanism 1940 and the locking mechanism 1930 are in a locked configuration relative to one another. The latch mechanism engagement component 1541 can be disengaged from the locking mechanism 1530, such that the latch mechanism 1540 and the locking mechanism 1530 are not in a locked configuration relative to one another. This can be accomplished by moving the latch mechanism in a latch release motion or distal direction, as indicated by arrow A. When actuating jaw lever 1920 and handle 1980 are forced or squeezed together, as shown in FIG. 19A, lever spring 1950 is compressed. When actuating jaw lever 1920 and handle 1980 are allowed to move away from one another, as shown in FIG. 19B, lever spring 1950 is uncompressed. In some embodiments, the lever spring 1950 can be referred to as a lever actuating torsion spring. In some embodiments, the lever actuating torsion spring is configured to bias the second jaw member away from the first jaw member. In some embodiments, the bias force of lever spring 1950 may operate to move actuating jaw lever 1920 away from handle 1980, for example about actuating jaw lever pivot 1922.

Figure 20C:
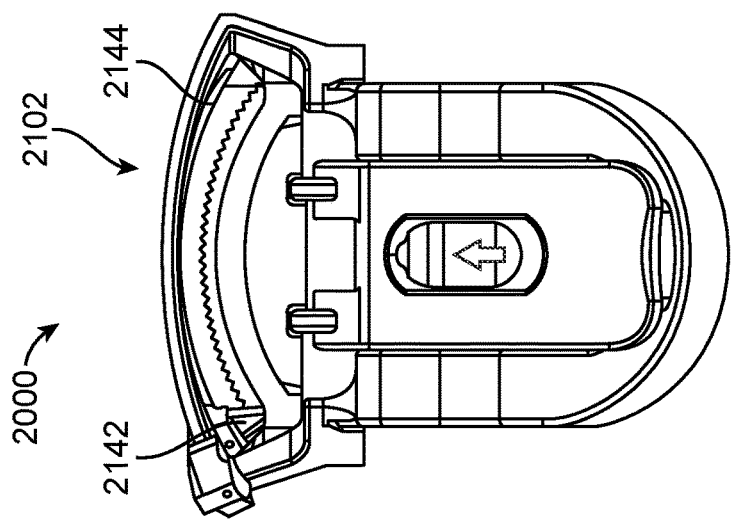
FIGS. 20A to 20C depict aspects of an excess skin removal and wound closure device, in accordance with some embodiments of the present invention.
Figure 20B:
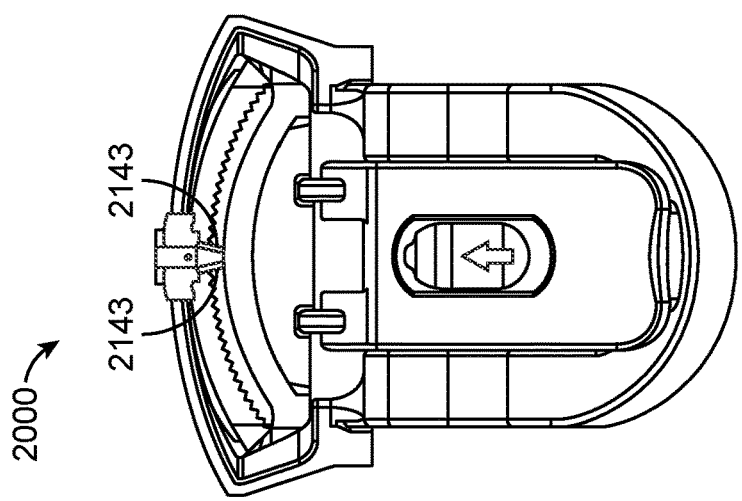
Figure 20A:
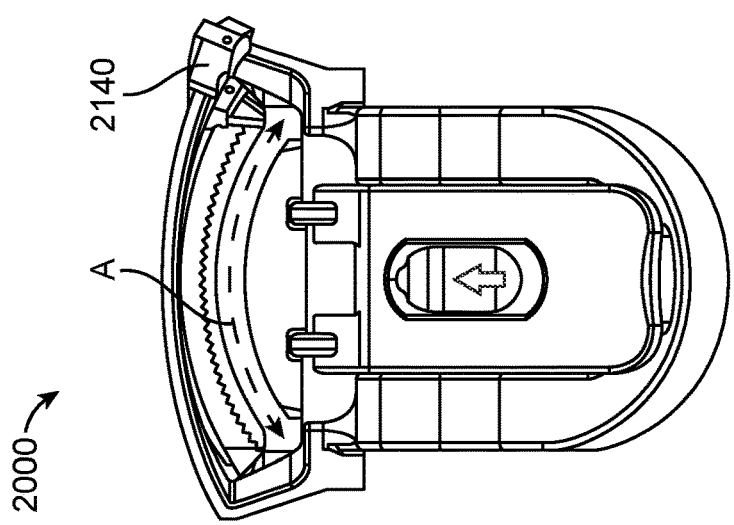

FIGS. 20A to 20C provide various illustrations of a blepharoplasty device 2000, according to embodiments of the present invention. As shown here, device 2000 can include a cutting mechanism 2140 having a cutting member or blade 2142. The cutting member 2142 can have one or more cutting edges 2143. The cutting mechanism 2140 can be a sliding cutting mechanism, and can slide from one side of the device to the opposite side of the device, and vice versa, for example in the directions indicated by arrow A. As shown here, blade 2142 can slide along or within blade guide 2144 of upper jaw 2102.

FIGS. 21A to 21C provide various illustrations of a blepharoplasty device 2100, according to embodiments of the present invention. As shown here, device 2000 can include a cutting mechanism 2240. The cutting mechanism 2240 can be a sliding cutting mechanism, and can slide from one side of the device to the opposite side of the device, and vice versa, for example in the directions indicated by arrow A.

Figures 22A, 22B:
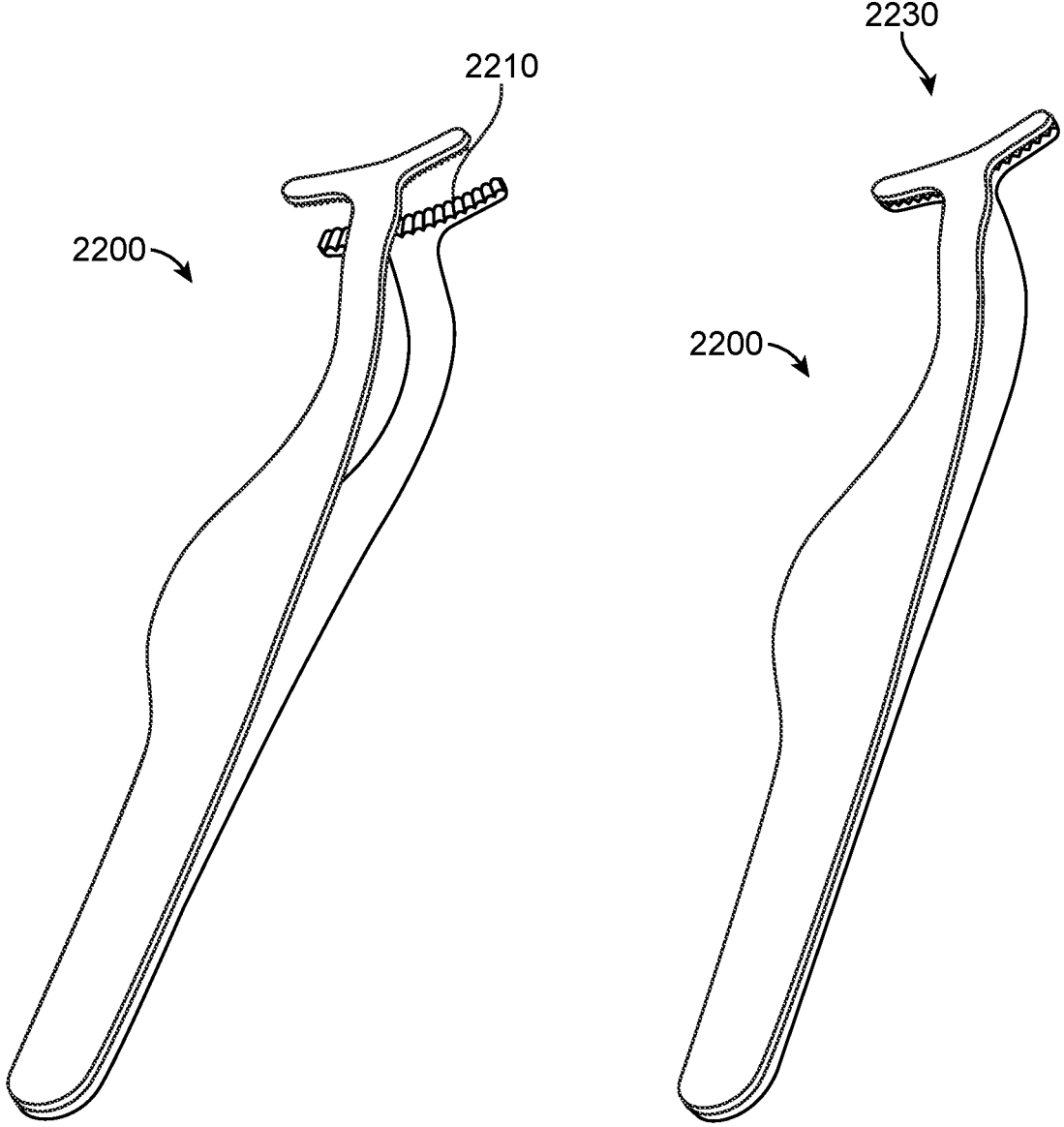
FIGS. 22A and 22B depict aspects of a grasping tool, in accordance with some embodiments of the present invention.

FIGS. 22A and 22B illustrate aspects of a grasping tool or forceps 2200 in an open position or configuration (FIG. 22A) and in a closed position or configuration (FIG. 22B). The grasping tool 2200 can include skin contact serrations 2210. The grasping tool can be used (e.g. by a surgeon or operator) to position patient tissue relative to a blepharoplasty device. For example, when a blepharoplasty device is in the open position, a portion of patient tissue can be positioned between the upper and lower jaws thereof. The grasping tool 2200 can be used to facilitate the movement of the tissue into the space between the upper and lower jaws.

For example, the grasping tool 2200 can grip upper eyelid tissue of a patient and pull it away from the patient and into the space between the upper and lower jaws. As shown here, the grasping tool or forceps 2200 provides a curved grasping surface 2230.

Figures 22C, 22D:
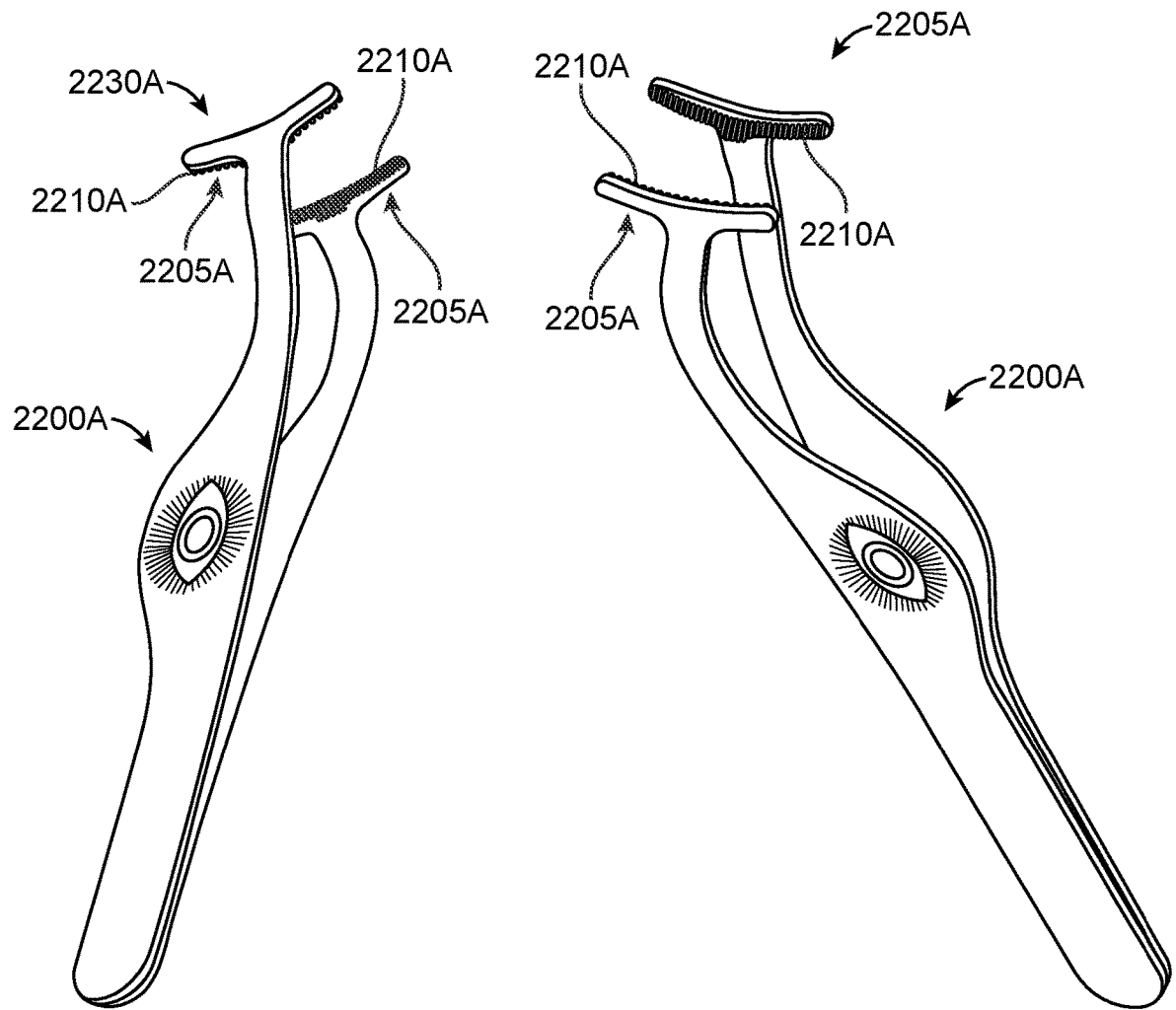
FIGS. 22C to 22E depict aspects of a grasping tool, in accordance with some embodiments of the present invention.
Figure 22E:
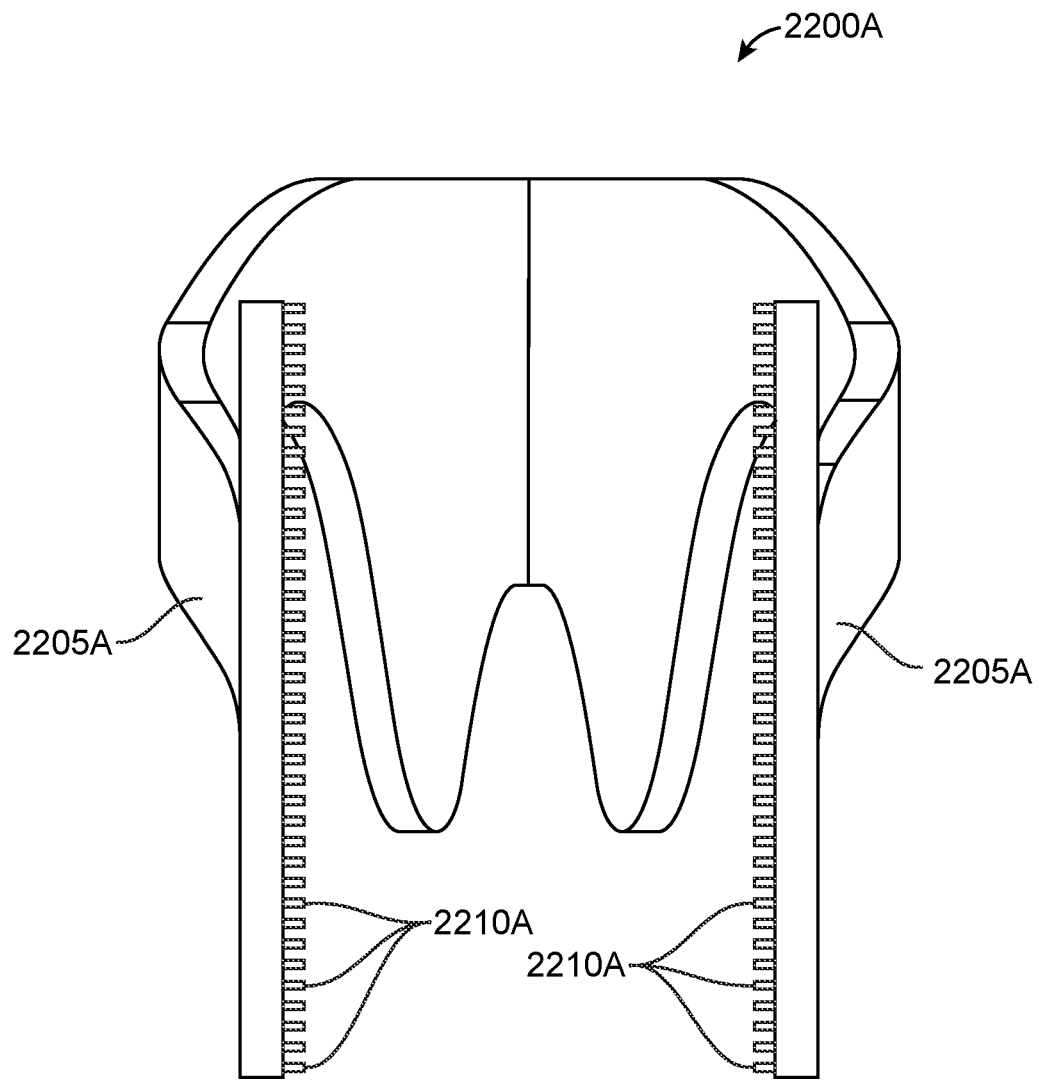

FIGS. 22C to 22E illustrate aspects of a grasping tool or forceps 2200A in an open position or configuration. The grasping tool 2200A can include microneedles 2210A at one or both of the distal ends 2205A thereof. In use, the microneedles can operate to sensitize the tissue to local topical anesthetics and/or to manipulate the tissue. The grasping tool can be used (e.g. by a surgeon or operator) to position patient tissue relative to a blepharoplasty device. For example, when a blepharoplasty device is in the open position, a portion of patient tissue can be positioned between the upper and lower jaws thereof. The grasping tool 2200A can be used to facilitate the movement of the tissue into the space between the upper and lower jaws. For example, the grasping tool 2200A can grip upper eyelid tissue of a patient and pull it away from the patient and into the space between the upper and lower jaws. As shown here, the grasping tool or forceps 2200A provides a curved grasping surface 2230.

Embodiments of the present invention can include kits having a skin grasping tool (e.g. forceps 2200 or 2200A), a local topical anesthetic agent, an incision bonding agent, a marker, and an iodine swab. The grasping tool (e.g. forceps 2200 or 2200A) can have an elongated body divided into two serrated tissue contacting surfaces at the distal end. The contacting surfaces can be curved comparable to the antero-posterior curve of the eyelid skin tissue. The distal end contacting surfaces can be adjustable between two distances, an open position (e.g. 8 mm) and a closed position (e.g. 0 mm). In some embodiments, the distance between surfaces is adjustable manually with compression. The serrations on the contacting surfaces can provide a shear force between the eyelid skin tissue and grasping tool allowing positioning of skin tissue through the jaws of the device component. The elongated body can include a section with a reduced width to fit through the open jaws of the device component. In operation, the skin grasping tool (e.g. forceps 2200 or 2200A) can fit through the device from the anterior direction and expands and compresses to grab or grasp and pull the tissue through.

Figure 23B:
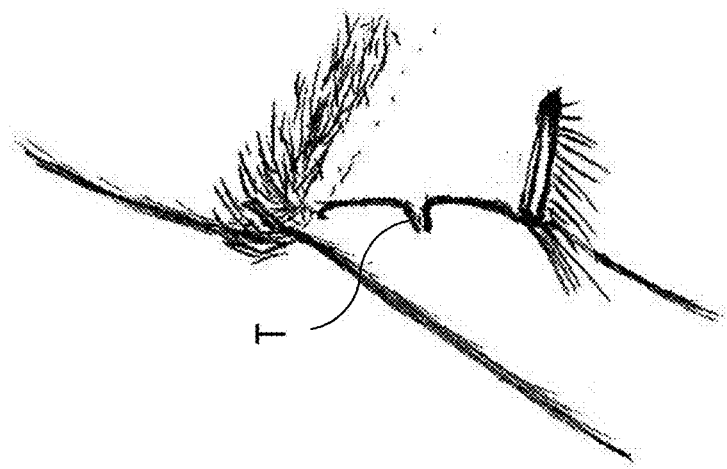
FIGS. 23A and 23B depict aspects of an excess skin removal and wound closure device, in accordance with some embodiments of the present invention.
Figure 23A:
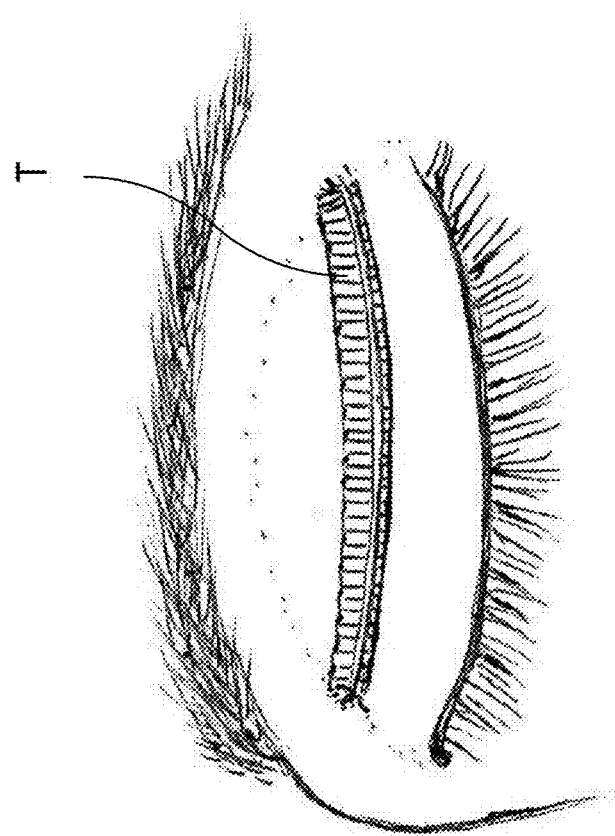

FIGS. 23A and 23B illustrate aspects of a blepharoplasty procedure, depicting the configuration of the eyelid tissue T after a clamp or device is released.

Exemplary treatment procedures can include marking the area of the eyelid tissue desired for removal with a marker and providing a local anesthetic to temporarily anesthetize the surgical area. After the surgical area is fully anesthetized, the surgical site can be disinfected with an iodine swab. The grasping tool can enter through the open jaws of the device, compress into the closed position, and grab or grasp the marked eyelid skin tissue area, then pull the tissue through the open jaws of the device. The device can then close fully clamping the tissue, cutting blood flow. A cutting mechanism can then be used to remove the eyelid skin tissue. After tissue is removed, an incision bonding agent can be applied on the incision, sealing it and allowing it to heal.

Any of the blepharoplasty systems, devices, kits, or methods disclosed herein may be used for any cosmetic skin removal (e.g. eyebrow, cheek, underarm, neck, and the like). In some embodiments, one or more components of a blepharoplasty device can be manufactured from a medical grade plastic. In some embodiments, one or more components of a blepharoplasty device (e.g. cutting blade components) can be manufactured from stainless steel or plastic. In some cases, a grasping tool or forceps can be manufactured from stainless steel or plastic.

In some embodiments, the width of the skin clamped has a value within a range from about 35 mm to about 45 mm. In some cases, the distance between jaws has a value within a range from about 0 mm to about 10 mm.

Advantageously, any of the blepharoplasty systems, devices, kits, or methods disclosed herein may be used in an office setting, thus avoiding hospital or surgery center fees and inconvenience. A local topical anesthetic can be temporary and targeted to the surgical region, thus avoiding systemic anesthesia. In some embodiments, the procedure after the local anesthetic takes around 10 minutes to complete. The device adjustability can allow adjustment of the amount of eyelid tissue to be removed, reducing asymmetry complication. Embodiments disclosed herein also can eliminate the need for sutures, and can reduce bruising, bleeding, and post operative recovery.

Although the preceding description contains significant detail in relation to certain preferred embodiments, it should not be construed as limiting the scope of the invention but rather as providing illustrations of the preferred embodiments.

Embodiments of the present invention encompass kits having a blepharoplasty system as disclosed herein. In some embodiments, the kit includes one or more blepharoplasty system components, along with instructions for using the device(s) for example according to any of the methods disclosed herein.

All features of the described systems and devices are applicable to the described methods mutatis mutandis, and vice versa.

Each reference provided herein in incorporated by reference in its entirety to the same extent as if each reference were individually incorporated by reference. Relatedly, all publications, patents, patent applications, journal articles, books, technical references, and the like mentioned in this specification are herein incorporated by reference to the same extent as if each individual publication, patent, patent application, journal article, book, technical reference, or the like was specifically and individually indicated to be incorporated by reference.

Although the foregoing invention has been described in some detail by way of illustration and example for purposes of clarity of understanding, one of skill in the art will appreciate that certain changes, modifications, alternate constructions, and/or equivalents may be practiced or employed as desired, and within the scope of the appended claims.

What is claimed is:

1. A device to excise excess skin and create wound closure, the device comprising:
   a base;
   a lever coupled with the base;
   a lock;
   an elongate, curved first jaw member that is fixed relative to the base and comprises a lower tissue contacting surface; and
   an elongate, curved second jaw member that is movable relative to the base and comprises an upper tissue contacting surface, wherein the upper tissue contacting surface faces toward the lower tissue contacting surface,
   wherein pivoting the lever causes linear movement of the second jaw member relative to the first jaw member, and wherein the lock is configured to fix the first jaw member relative to the second jaw member.

2. The device of claim 1, wherein the lower tissue contacting surface is serrated, and wherein the upper tissue contacting surface is serrated.

3. The device of claim 1, wherein the lever is coupled with the base via a lever pivot.

4. The device of claim 1, wherein the lock is releasably engageable with the second jaw member.

5. The device of claim 1, wherein the lock is coupled with the base via a locking pivot.

6. The device of claim 1, further comprising a latch, wherein the lock is releasably engageable with the latch.

7. The device of claim 6, wherein the lock releasably engages the latch within the base.

8. The device of claim 6, wherein the latch is coupled with the second jaw member.

9. The device of claim 6, further comprising a spring that is compressible between the latch and the base.

10. The device of claim 9, wherein the spring biases engagement of the latch against the lock.

11. The device of claim 1, wherein the lock is coupled with the lever.

12. The device of claim 1, further comprising a pawl in fixed relationship with the second jaw member, wherein the lock comprises engagement teeth configured to releasably engage the pawl.

13. The device of claim 12, further comprising a spring configured to bias the engagement teeth of the lock against the pawl.

14. The device of claim 1, wherein at least one of the first jaw member or the second jaw member has a silicone coating.

15. The device of claim 1, further comprising a spring configured to bias the second jaw member away from the first jaw member.

16. The device of claim 1, further comprising a torsion spring configured to bias the second jaw member away from the first jaw member.

17. The device of claim 1, wherein at least one of the first jaw member or the second jaw member comprises a tissue contacting side having a contoured surface with a shape that is customized to an anatomy of a patient based on an imaging scan of the patient.

18. An excess skin removal and wound closure device, the device comprising:
- a base;
- a lever coupled with the base via a lever pivot;
- a lock;
- an elongate, curved first jaw member fixed relative to the base and having a lower serrated tissue contacting surface; and
- an elongate, curved second jaw member in pivoting relationship with the lever and having an upper serrated tissue contacting surface, the upper serrated tissue contacting surface facing toward the lower serrated tissue contacting surface,
- wherein the lock is releasably engageable with a support assembly of the first jaw member, and
- wherein pivoting the lever causes linear movement of the second jaw member relative to the first jaw member.

19. The device of claim 18, wherein the lock comprises a first set of engagement teeth and a second set of engagement teeth that releasably engage the support assembly of the first jaw member.

20. The device of claim 18, wherein the lock comprises a serpentine section that enables compression of the lock.

21. The device of claim 18, further comprising a spring coupled with the base and the lever.

22. The device of claim 18, wherein the support assembly of the first jaw member is releasably engageable with the base.

23. The device of claim 18, wherein the lock comprises one or more compression tabs.

* * * * *